(12) United States Patent
Kumar et al.

(10) Patent No.: US 9,763,911 B2
(45) Date of Patent: Sep. 19, 2017

(54) PROSTACYCLIN COMPOSITIONS FOR REGULATION OF FRACTURE REPAIR AND BONE FORMATION

(71) Applicant: MAYO FOUNDATION FOR MEDICAL EDUCATION AND RESEARCH, Rochester, MN (US)

(72) Inventors: Rajiv Kumar, Rochester, MN (US); Jennifer J. Westendorf, Rochester, MN (US); Theodore A. Craig, Rochester, MN (US); Zachary C. Ryan, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 14/563,754

(22) Filed: Dec. 8, 2014

(65) Prior Publication Data

US 2015/0164853 A1    Jun. 18, 2015

Related U.S. Application Data

(60) Provisional application No. 61/915,116, filed on Dec. 12, 2013.

(51) Int. Cl.
| | |
|---|---|
| *A61K 9/00* | (2006.01) |
| *A61K 31/00* | (2006.01) |
| *A61K 31/343* | (2006.01) |
| *A61L 31/16* | (2006.01) |
| *A61L 31/10* | (2006.01) |
| *A61K 45/06* | (2006.01) |
| *A61L 27/34* | (2006.01) |
| *A61L 27/54* | (2006.01) |

(52) U.S. Cl.
CPC ............ *A61K 31/343* (2013.01); *A61K 45/06* (2013.01); *A61L 27/34* (2013.01); *A61L 27/54* (2013.01); *A61L 31/10* (2013.01); *A61L 31/16* (2013.01); *A61L 2300/22* (2013.01); *A61L 2300/602* (2013.01); *A61L 2300/606* (2013.01)

(58) Field of Classification Search
CPC ....... A61K 31/343; A61K 45/06; A61L 31/10; A61L 31/16; A61L 2300/22; A61L 2300/602; A61L 2300/606; A61L 27/34; A61L 27/54
See application file for complete search history.

(56) References Cited

U.S. PATENT DOCUMENTS

| | | | | |
|---|---|---|---|---|
| 6,716,444 B1 * | 4/2004 | Castro | .................... | A61L 27/306 424/400 |
| 6,953,560 B1 * | 10/2005 | Castro | ........................ | A61F 2/82 423/423 |
| 6,998,134 B2 * | 2/2006 | Schmidmaier | .......... | A61L 27/34 424/422 |
| 7,547,715 B2 * | 6/2009 | Sakai | .................... | A61K 9/1647 514/353 |
| 8,114,152 B2 * | 2/2012 | Furst | ......................... | A61F 2/91 606/108 |
| 8,114,427 B2 * | 2/2012 | Schmidmaier | .......... | A61L 27/34 424/422 |
| 8,313,760 B2 * | 11/2012 | Hunter | .................... | A61L 27/54 424/422 |
| 8,436,026 B2 * | 5/2013 | Sakai | .................... | A61K 9/1647 514/353 |
| 8,580,800 B2 | 11/2013 | Von Nussbaum et al. | | |
| 8,642,630 B2 * | 2/2014 | Sakai | .................... | A61K 9/1647 514/353 |
| 2003/0139372 A1 | 7/2003 | Scutt et al. | | |
| 2004/0171692 A1 | 9/2004 | Andrew et al. | | |
| 2005/0101673 A1 | 5/2005 | Norden et al. | | |
| 2005/0107870 A1 * | 5/2005 | Wang | ...................... | A61L 31/10 623/1.44 |
| 2006/0252045 A1 * | 11/2006 | Chatterjee-Kishore | ............... | C12Q 1/6876 435/6.13 |
| 2009/0130113 A1 | 5/2009 | Kneissel et al. | | |

FOREIGN PATENT DOCUMENTS

WO    2008115732 A2    9/2008

OTHER PUBLICATIONS

Balemans, W. et al., "Increased Bone Density in Sclerosteosis is Due to the Deficiency of a Novel Secreted Proten (SOST)", Human Molecular Genetics, 2001, vol. 10, No. 5, 537-543.
Huan-Qing-Yang, et al., "The—9247 T/C Polymorphism in the SOST Upstream Regulatory Region That Potentially Affects C/EBPa and FOXA1 Binding is Associated with Osteoporosis", Bone 45, 2009, 289-294, Elsevier.
Balemans et al., "Identification of a 52 kb deletion downstream of the SOST gene in patients with van Buchem disease", J. Med. Genet, 2002, 39:91-97.
Blackwell et al., "Prostaglandins in Bone: Bad Cop, Good Cop?", Trends Endocrinol Metab., 2010; 21(5):294-301.
Boyden et al., "High Bone Density Due to a Mutation in LDL-Receptor—Related Protein 5", New England Journal of Medicine, 2002, 20, vol. 346.
Burge et al., "Incidence and Economic Burden of Osteoporosis-Related Fractures in the United States, 2005-2025", Journal of Bone and Mineral Research, vol. 22, No. 3, 2007.
CCooper et al., "Secular Trends in the Incidence of Hip and Other Osteoporotic Fractures", Osteoporos Int. May 2011, 22(5), 1277-1288.

(Continued)

*Primary Examiner* — Robert A Wax
*Assistant Examiner* — Olga V Tcherkasskaya
(74) *Attorney, Agent, or Firm* — Edwin S. Flores; Chalker Flores, LLP

(57) ABSTRACT

The present disclosure provides a prostacyclin coated implant to enhance fracture repair and bone formation comprising: an implant; and a prostacyclin coating comprising a prostacyclin compound disposed in a polymer coating the implant, wherein the prostacyclin coating releases the prostacyclin compound which enhances fracture repair and bone formation.

10 Claims, 7 Drawing Sheets

(56) References Cited

OTHER PUBLICATIONS

Craig, T et al., "Sclerostin-erbB-3 Interactions: Modulation of ErbB-3 Activity by Sclerostin", Biochem Biophys Res Commun. 2010, 12; 402(2); 421-424.

Craig, T et al., "Sclerostin Binds and Regulates the Activity of Cysteine Rich Protein 61", Biochem Biophys Res Commun. Jan. 29; 392(1): 36.

Devarajan-Ketha et al., "The Sclerostin-Bone Protein Interactome", Biochem Biophys Res Commun. Jan. 13, 2012; 417(2): 830-835.

FitzGerald, G., "COX-2 and Beyond: Approaches to Prostaglandin Inhibition in Human Disease", Nature Reviews/Drug Discovery, vol. 2, 2003, 879.

Gong, Y et al., "LDL Receptor-Related Protein 5 (LRP5) Affects Bone Accrual and Eye Development", Cell, vol. 107, 513-523, Nov. 16, 2001.

Jee, W.S. et al., "Prostaglandin E2 Enhances Cortical Bone Mass and Activates Intracortical Bone Remodeling in Intact and Ovariectomized Female Rats", Bone, 11, 253-266, 1990.

Kamiya, N. et al., "BMP signaling negatively regulates bone mass through sclerostin by inhibiting the canonical Wnt pathway", Development 135, 3801-3811 (2008), Development and Disease.

Kusu, N et al., "Sclerostin Is a Novel Secreted Osteoclast-derived Bone Morphogenetic Protein Antagonist with Unique Ligand Specificity", The Journal of Biological Chemistry, vol. 278, No. 26, pp. 24113-24117, 2003.

Leibson, C. et al., "The Journal of Biological Chemistry vol. 278, No. 26, Issue of Jun. 27, pp. 24113-24117, 2003", JAGS, Oct. 2002, vol. 50, No. 10.

Li X et al., "Targeted Deletion of the Sclerostin Gene in Mice Results in Increased Bone Formation and Bone Strength" Journal of Bone and Mineral Research, vol. 23, No. 6, 2008.

Little, R. et al., "A Mutation in the LDL Receptor-Related Protein 5 Gene Results in the Autosomal Dominant High-Bone-Mass Trait", Am. J. Hum. Genet. 70:11-19, 2002.

Moncada, S. et al., "An Enzyme Isolated from Arteries Transforms Prostaglandin Endoperoxides to an Unstable Substance that Inhibits Platelet Aggregation", Nature, vol. 263, 21, 1976.

Nagel D. et al., "1a,25-Dihydroxyvitamin D3 Increases TGF B1 Binding to Human Osteoblasts", Biochemical and Biophysical Research Communications 290, 1558-1563 (2002).

Pederson, L et al., "Regulation of bone formation by osteoclasts involves Wnt/BMP signaling and the chemokine sphingosine-1-phosphate", 20764-20769, PNAS, Dec. 30, 2009, vol. 105, No. 52.

Raisz, L., "Complement-Dependent Stimulation of Prostaglandin Synthesis and Bone Resorption", 1974. Departments of Pharmacology and Toxicology and Medicine, University of Rochester School of Medicine and Dentistry, Rochester, New York 14642.

Ryan, Z. et al., "Sclerostin alters serum vitamin D metabolite and fibroblast growth factor 23 concentrations and be urinary excretion of calcium", PNAS, Apr. 9, 2013, vol. 110, No. 15, 6199-6204.

Ryan, Z. C. et al., "Enhanced Prostacyclin Production is Associated with High Bone Mass in Sclerostin Deficiency." Science, Submitted Manuscript: Confidential, Dec. 27, 2011, pp. 1-6.

Samuelsson, B. et al., "Prostaglandins and Thromboxanes", Ann. Rev. Biochem. 1978.47:997-1029.

Stern, A et al., "Isolation and culture of primary osteocytes from the long bones of skeletally mature and aged mice", Biotechniques. Jun. 2012; 52(6): 361-373.

Van Wesenbeeck L et al., "Six Novel Missense Mutations in the LDL Receptor-Related Protein 5 (LRP5) Gene in Different Conditions with an Increased Bone Density", Am. J. Hum. Genet. 72:763-771, 2003.

Wrinkler D. et al., "Osteocyte control of bone formation via sclerostin, a novel BMP antagonist", The EMBO Journal vol. 22, No. 23 pp. 6267-6276, 2003.

Yasuda, Hisataka et al., "Osteoclast differentiation factor is a ligand for osteoprotegeriny osteoclastogenesis-inhibitory factor and is identical to TRANCEyRANKL", Proc. Natl. Acad. Sci. USA, vol. 95, pp. 3597-3602, Mar. 1998 Cell Biology.

Yoshida Factor H et al., "The Murine Mutation Osteopetrosis is in the Coding Region of the Macrophage Colony Stimulating Factor Gene", Letters to Nature, vol. 345, 6274, pp. 442-444, 1990.

* cited by examiner

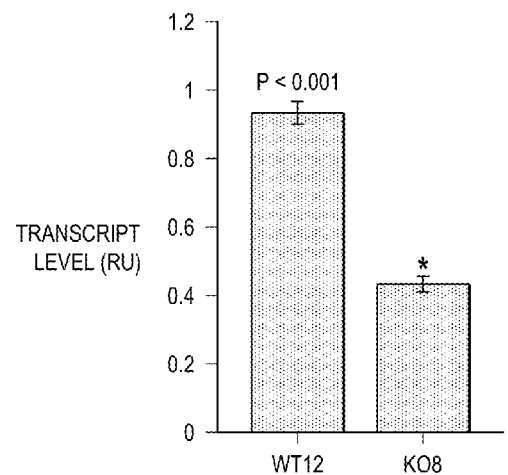
FIG. 5B
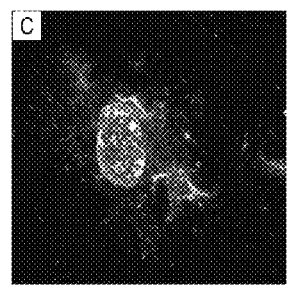 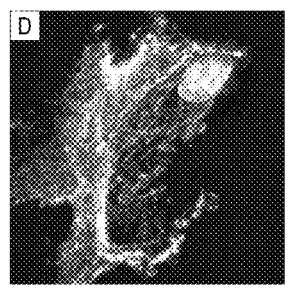
FIG. 5C    FIG. 5D
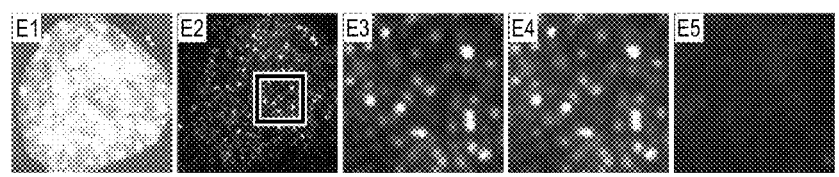
FIG. 5E
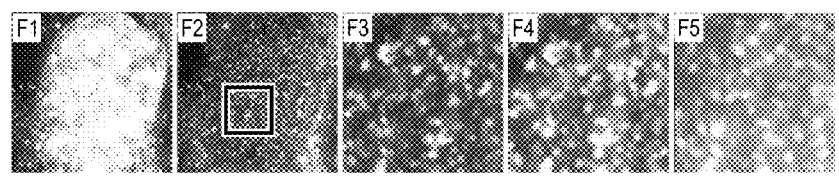
FIG. 5F

SEQUENCE LISTING

```
<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
ccgggaacta ctgcaaaaat                                           20

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ccaaggtttt caatgatgct t                                         21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ggttttgacc ttgtgggaaa                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
```

```
catattggga tgcgattcct                                              20

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
tatggatctc cacggcaac                                               19

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
gtccactggc ggaacttg                                                18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ctgccagaga acaagtgcaa                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
aatggcacca ttgaccctaa                                              20

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
cagtgttgtt ctgggttttg g                                            21

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
acctggggtc acaatatcat ct                                           22

<210> SEQ ID NO 11
<211> LENGTH: 21
<212> TYPE: DNA
```

```
<213> ORGANISM: Artificial Sequence
<220> FEATURE:
<223> OTHER INFORMATION: Synthetic primer

<400> SEQUENCE: 11
cgtgtcagca aagcttcttt t                                              21

<210> SEQ ID NO 12
<211> LENGTH: 18
<212> TYPE: DNA
<213> ORGANISM: Artificial Sequence
<220> FEATURE:
<223> OTHER INFORMATION: Synthetic primer

<400> SEQUENCE: 12
ggctcacgtc gctcatct                                                  18

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tcctgagaac aaccagacca                                                20

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gcagctgtac tcggacacat c                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tgcttcccaa tcctatttgc                                                20

<210> SEQ ID NO 16
<211> LENGTH: 18
<212> TYPE: DNA
<213> ORGANISM: Artificial Sequence
<220> FEATURE:
<223> OTHER INFORMATION: Synthetic primer

<400> SEQUENCE: 16
agctcagggg gaatcgag                                                  18

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
aggcacggca aaaacagtat                                                20
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
tgtggcattt ggcatcaata                                           20

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
catgaaagca aggcgcata                                            19

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
catctacgca gttctggttg g                                         21

<210> SEQ ID NO 21
<211> LENGTH: 21
<212> TYPE: DNA
<213> ORGANISM: Artificial Sequence
<220> FEATURE:
<223> OTHER INFORMATION: Synthetic primer

<400> SEQUENCE: 21
cgccaccaag acctacatac g                                         21

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
acatgaccga gccgatctgt                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
cctctttcca ggagctcaca                                           20

<210> SEQ ID NO 24
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 24
tcgatgtcac cgtacagctc                                          20

<210> SEQ ID NO 25
<211> LENGTH: 19
<212> TYPE: DNA
<213> ORGANISM: Artificial Sequence
<220> FEATURE:
<223> OTHER INFORMATION: Synthetic primer

<400> SEQUENCE: 25
gatgctcttc cgagctgtg                                           19

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
ggattggaac agcaaggatt t                                        21

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tgcagatctt ggactggaca                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
aagaacggta gctgggatca                                          20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer

<400> SEQUENCE: 29
gactgtgacg aggagttcca g                                        21

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
gagctccacc gttgtctcac                                          20

```
<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
gtgaggggct ttattccaca                                              20

<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32 gaaacccca cctgaacc                                                 18

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
ccaactacag tcccgtggag                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
ttggaagttc agagccacaa                                              20

<210> SEQ ID NO 35
<211> LENGTH: 22
<212> TYPE: DNA
<213> ORGANISM: Artificial Sequence
<220> FEATURE:
<223> OTHER INFORMATION: Synthetic primer

<400> SEQUENCE: 35
cgctgtgtat gaaaagatcg tg                                           22

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
gtgcctatgc tgtgcaagtg                                              20

<210> SEQ ID NO 37
<211> LENGTH: 21
<212> TYPE: DNA
<213> ORGANISM: Artificial Sequence
<220> FEATURE:
<223> OTHER INFORMATION: Synthetic primer
```

<400> SEQUENCE: 37
ggctcctgga cactacacct a                                    21

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
atagttggcc tccaccactg                                      20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
gcacactgct ggtcatcaag                                      20

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
acgtttcagc gcatcctc                                        18

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
atgccatcaa cagcatcaaa                                      20

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
aaactcagga acctctgtgt cc                                   22

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
ccctccaccc tatgacaaga                                      20

<210> SEQ ID NO 44
<211> LENGTH: 19

```
<212> TYPE: DNA
<213> ORGANISM: Artificial Sequence
<220> FEATURE:
<223> OTHER INFORMATION: Synthetic primer

<400> SEQUENCE: 44
gccccaggta agcaaactt                                              19

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ggatgtaccc accagctttc                                             20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
acctgcaggg atacgttgtc                                             20

<210> SEQ ID NO 47
<211> LENGTH: 19
<212> TYPE: DNA
<213> ORGANISM: Artificial Sequence
<220> FEATURE:
<223> OTHER INFORMATION: Synthetic primer

<400> SEQUENCE: 47
gcactgagac acgggaaga                                              19

<210> SEQ ID NO 48
<211> LENGTH: 19
<212> TYPE: DNA
<213> ORGANISM: Artificial Sequence
<220> FEATURE:
<223> OTHER INFORMATION: Synthetic primer

<400> SEQUENCE: 48
gtctctgcct cccaagctc                                              19

<210> SEQ ID NO 49
<211> LENGTH: 8
<212> TYPE: DNA
<213> ORGANISM: Artificial Sequence
<220> FEATURE:
<223> OTHER INFORMATION: Synthetic primer

<400> SEQUENCE: 49 cctttgat                                                           8
```

PROSTACYCLIN COMPOSITIONS FOR REGULATION OF FRACTURE REPAIR AND BONE FORMATION

CROSS-REFERENCE TO RELATED APPLICATIONS

This non-provisional Patent Application claims priority to U.S. Provisional Patent Application Ser. No. 61/915,116, filed Dec. 12, 2013, entitled "PROSTACYCLIN COMPOSITIONS FOR REGULATION OF FRACTURE REPAIR AND BONE FORMATION," the contents of which is incorporated by reference herein in its entirety

TECHNICAL FIELD OF THE INVENTION

The present invention relates generally to methods and compositions of prostacyclin and derivatives for the production of a pharmaceutical agent for treating and enhancing fracture repair and bone formation.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with treating and enhancing fracture repair and bone formation.

The skeleton provides a number of functions, such as the provision of support, the protection of internal organs and the provision of sites for the attachment of muscles and tendons which operatively function to enable an animal to move. Bone is a living tissue which is being constantly resorbed, replaced and remodeled during growth and development. This is particularly relevant during skeleton development and fracture repair. When the adult skeleton is formed it requires constant maintenance to ensure its functions are adequately maintained.

The deposition, resorption and/or remodeling of bone tissue is undertaken by specialized, anabolic cells known as osteoblasts (involved in bone tissue deposition) and resorptive cells, known as osteoclasts (involved in the resorption of bone tissue). Osteocytes produce a number of factors that influence bone formation and resorption. The activity of these specialized cells varies during growth and development. During normal, early human development, new bone tissue is formed faster than old bone is resorbed, resulting in bone becoming larger, heavier and more dense. In the fully developed human adult, peak bone density mass is achieved during the late 20's. However, in later life, osteoclast activity exceeds that of osteoblasts, resulting in a decrease in bone density and, consequently, a reduction in bone mass.

Bone loss results in demineralizing disorders such as osteoporosis and enhances the susceptibility to fractures that are responsible for significant morbidity, mortality and excess health care costs. With the anticipated aging of the U.S. population, admissions for fractures are anticipated to rise with attendant costs of $25 billion per year by 2025. New strategies aimed at increasing bone mass are needed to address the significant costs and co-morbidities associated with osteoporosis and fractures, particularly in the aging population.

U.S. Patent Application Publication No. 2005/0101673, entitled, "Use of Orally Available Prostacyclin Derivatives for the Production of a Pharmaceutical Agent for Treating Diseases that are Associated with Bone Marrow Edemas," discloses the use of orally available prostacyclin derivatives for the production of a pharmaceutical agent for treating diseases that are associated with bone marrow edemas.

U.S. Patent Application Publication No. 2003/0139372, and U.S. Patent Application Publication No. 2004/0171692 both entitled, "Modulation of Bone Formation" discloses the use of an activator or ligand of a peroxisome proliferator-activated receptor, other than PPARγ, or pharmaceutically acceptable derivative of said activator or ligand, in the manufacture of a medicament for the treatment or prophylaxis of bone disease allows, for the first time, bone anabolism to enhance the deposition of bone in conditions which would benefit from increased bone deposition. The reverse, where there is inhibition and/or retardation of bone deposition is also facilitated.

U.S. Pat. No. 8,580,800, entitled "1,4-diaryl-pyrimidopyridazine-2,5-diones and their use" discloses 1,4-diarylpyrimido[4,5-d]pyridazine-2,5-dione derivatives for the treatment and/or prevention of diseases and also to their use for preparing medicaments for the treatment and/or prevention of diseases, in particular for the treatment and/or prevention of disorders of the lung and the cardiovascular system.

SUMMARY OF THE INVENTION

The present disclosure provides a method for treating and/or enhancing fracture repair and bone formation by providing a fracture; providing an implant having a prostacyclin coating comprising a prostacyclin compound disposed in a polymer; and positioning the implant to provide prostacyclin at the fracture site, wherein the prostacyclin coating releases the prostacyclin compound about the bone healing interface to enhance fracture repair and bone formation. The implant may be a cage, a wire, a staple, a plate, a screw, a rod, a tubular structure, a scaffold, an external fixation device or a combination thereof and made of stainless steel, titanium, polyether ether ketone, polyethelene, and combinations thereof. The polymer may be an extended release polymer that provides a release of the prostacyclin compound over less than 6 months and may include multiple layers to provide a specific release regime over an extended period of time. The prostacyclin compound is (Z)-5-[(4R,5R)-5-hydroxy-4-((S,E)-3-hydroxyoct-1-enyl)hexahydro-2H-cyclopenta[b]furan-2-ylidene]pentanoic acid but may also include derivatives, mimics and analogues thereof.

The present disclosure provides a prostacyclin coated implant to enhance fracture repair and bone formation comprising: an implant; and a prostacyclin coating comprising a prostacyclin compound disposed in a polymer coating the implant, wherein the prostacyclin coating releases the prostacyclin compound which enhance fracture repair and bone formation.

The polymer coating may be an extended release polymer that provides a release of the prostacyclin compound over less than 6 months and/or include multiple layers of polymer coatings to provide a specific release regime over an extended period of time. The implant may be made of a biodegradable polymer in instances where the implant is not used to stabilize a fracture.

The present disclosure provides a bone scaffold implant for accelerating bone healing comprising a scaffold implant containing a prostacyclin compound for release to enhance bone formation about the scaffold implant.

The prostacyclin compound may be disposed in an extended release polymer to provide a release of the prostacyclin compound over months. The prostacyclin compound may include multiple layers positioned one over the other to provide a specific release regime over an extended period of time an may be used in conjunction with antibiotics and other infection control compositions, e.g., silver ions, zinc ions, or silver ions and zinc ions to prevent or treat infection.

BRIEF DESCRIPTION OF THE DRAWINGS

For a more complete understanding of the features and advantages of the present invention, reference is now made to the detailed description of the invention along with the accompanying figures and in which:

FIGS. 5A-5F shows Enhanced b-catenin and b-catenin-associated transcription is present in clonal osteocytes from Sost KO mice. FIGS. 5A and 5B show total β-catenin was increased 583%, and non-phosphorylated active β-catenin was increased 872% in Sost KO OC clone vs. Sost WT OC clone. FIG. 5C shows an increase in β-catenin present in euchromatin of Sost KO OC clone 8. FIG. 5D shows nuclear β-catenin co-localized with LEF over areas of euchromatin in Sost KO OC clone 8. FIG. 5E, panels 1-5 the localization of β-catenin in the nucleus of a clonal Sost WT osteocyte, and in FIG. 5F, panels 1-5, localization of β-catenin in the nucleus of a clonal Sost KO osteocyte is shown (red color).

DETAILED DESCRIPTION OF THE INVENTION

Figure 1A:
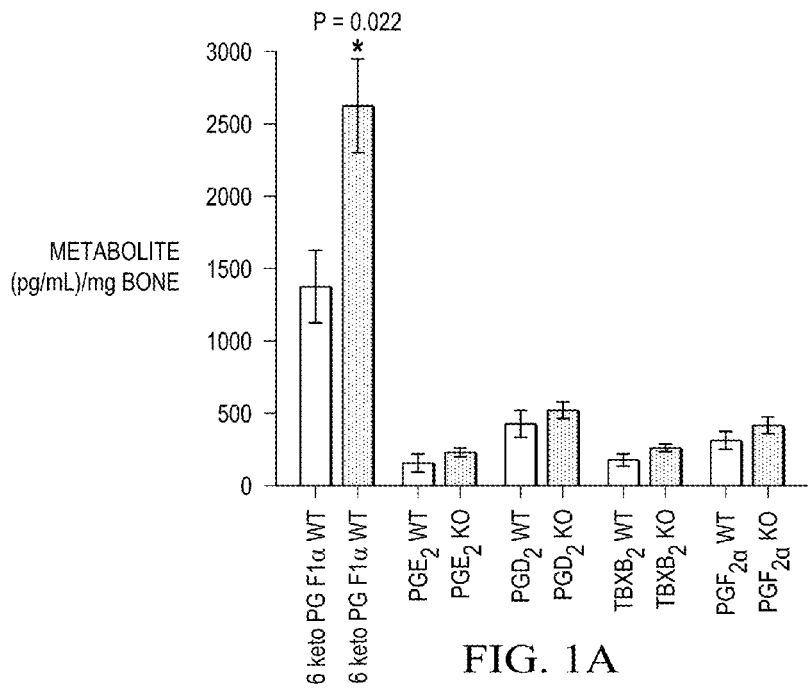
FIG. 1A-C show prostaglandin concentrations, mRNAs for prostaglandin synthases, and prostacyclin synthase in osteocytes in extracts of bones, or decalcified bone sections from Sost WT or KO mice.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "about" or "approximately" mean that the parameter so modified need not be exactly the value or range of values stated herein to still come within the scope of this invention. While circumstances and the knowledge of those skilled in the art may require an even greater departure from the indicated value or range of values, at a minimum "about" or "approximately" is to be construed to be at least .+-.15% of the value so modified, in some embodiments at least plus or minus 5% of the value.

As used herein, "biocompatible" refers to an intact polymer and to its biodegradation products all of which are not, or at least are minimally, toxic to living tissue; do not, or at least minimally and reversibly, injure living tissue; and/or do not, or at least minimally and/or controllably, cause an immunological reaction in living tissue.

As used herein, "biodegradable" refers to the in vivo cleaving of bonds in a polymer that link the monomer-derived portions together resulting in the break-down of the polymer into smaller and smaller fragments until the fragments are small enough to be either absorbed and metabolized or excreted by the organism. The primary mechanism of biodegradation for some embodiments of this invention is enzyme-catalyzed hydrolysis of ester groups.

As used herein, "bone," refers to bone that is cortical, cancellous or cortico-cancellous of autogenous, allogenic, xenogenic, or transgenic origin.

As used herein, "coating" refers to a single layer or to multiple layers of a substance or substances disposed over a surface of an implantable medical device. It will be readily apparent to those skilled in the art which meaning of coating is intended in any particular aspect of the invention described herein based on the context.

As used herein, to "dispose" a layer on a surface means to form a layer of a polymer over the surface of an implantable medical device or over the surface formed by a previously disposed layer. The layer can be formed by any means presently known or as such may become known in the future including at present, without limitation, spraying, dipping, electrodeposition, roll coating, brushing, direct droplet application and molding.

As used herein, a "surface" of an implantable medical device, a bone or a bone fragment refers to an outer surface, that is a surface that is directly in contact with the external environment and/or an inner surface if the device comprises a lumen and/or the edge of the device that connects the outer surface with the lumen. Unless expressly stated to be otherwise, "surface" will refer to all or any combination of the preceding.

As used herein, "optional" or "optionally" when used to modify an element of this invention means that the element may be present or it may not be present and both are within the ambit of this invention.

As used herein, "Osteoconductive," refers to the ability of a non-osteoinductive substance to serve as a suitable template or substance along which bone may grow.

As used herein, "Osteogenic," refers to the ability of an agent, material, or implant to enhance or accelerate the growth of new bone tissue by one or more mechanisms such as osteogenesis, osteoconduction, and/or osteoinduction.

As used herein, "Osteoinductive," refers to the quality of being able to recruit cells from the host that have the potential to stimulate new bone formation. Any material that can induce the formation of ectopic bone in the soft tissue of an animal is considered osteoinductive.

As used herein, "immediate release" refers to describe a release profile to effect delivery of an active as soon as possible, that is, as soon as practically made available to an animal, whether in active form, as a precursor and/or as a metabolite. Immediate release may also be defined functionally as the release of over 80 to 90 percent (%) of the active ingredient within about 1, 60, 90, 100 or 120 hours or less.

As used herein, "extended release" and "delayed release" refers a release profile to effect delivery of an active over an extended period of time. Extended release may also be defined functionally as the release of over 80 to 90 percent (%) of the active ingredient after about 1 day and about 1, 2, 4, 6 or even 8 weeks. Extended release as used herein may also be defined as making the active ingredient available to the patient or subject regardless of uptake, as some actives may never be absorbed by the animal.

In instances where one or more bones are fractured, the fracture is set, immobilized and stabilized so that the bones can undergo fibrocartilaginous callus formation, bone callus formation, and bone remodeling. However, it is often necessary for bone fractured repair using medical implants (i.e., plates, nails, screws, or pins) in addition it may be necessary to use bone grafts to allow for proper healing or to assist in the healing process. In addition, there are instances where the healing and repair process must be supplemented using additional mechanisms to stimulate bone growth, e.g., electrical stimulation of fracture site, ultrasound treatment, free vascular fibular graft techniques, and/or bone substitutes. The present invention provides compositions and methods of treating and enhancing fracture repair and bone formation by increasing the concentration of prostacyclin locally to stimulate bone formation, growth and healing. In general, the present invention can be used in treating and enhancing fracture repair and bone formation of any bone in conjunction with the bone repair methods and devices currently used in the art that repair, mend, change the shape, pull together or compress bone throughout the skeletal system.

In one embodiment the prostacyclin compositions may be prostacyclin or a pharmaceutical composition comprising prostacyclin. However, the present invention also includes prostacyclin derivatives, prostacyclin analogues, prostacyclin mimics and the like. In addition, the prostacyclin compositions may be precursors of prostacyclin compositions that can be formed in to the active prostacyclin composition locally. In addition, the prostacyclin composition may function to indirectly increase the concentration of prostacyclin by decreasing the metabolism of prostacyclin or by affecting the pathways to increase the availability of prostacyclin. The pharmaceutical composition may include multiple approaches to increase the local prostacyclin concentration, e.g., the pharmaceutical composition may include prostacyclin and an active agent to decrease the degradation of the prostacyclin and provide an increased concentration locally.

The present invention provides a pharmaceutical prostacyclin composition that is applied as a coating to an implant used at a bone repair site. The implant may be configured to align, biopsy, fuse, and/or stabilize a bone and may be a bone screw wires, screws, staples, rods, plates, screws, washers, cylindrical cages, external fixators and combinations of these devices. In addition the present invention can be used with shape changing cages that are used to pull together and compress bone segments. The implant can be constructed in part or entirely from stainless steel, titanium, or a combination thereof. In addition, the bone implant can include a shape memory metal, an elastic biocompatible metal, an elastic biocompatible polymer, or a combination thereof. The implant can also be synthetic and include polyether ether ketone (PEEK), polyethelene, or a combination thereof.

A coating containing pharmaceutical composition may be coated onto the implant prior to implantation. The coating serves to increase prostacyclin concentration locally for treating and enhancing fracture repair and bone formation. The pharmaceutical composition may include prostacyclin derivatives, prostacyclin analogues, prostacyclin mimics and the like or prostacyclin precursors that can be formed into active prostacyclin compositions locally. In addition, coating may actually be multiple coatings of the same pharmaceutical composition or different pharmaceutical compositions to enhancing fracture repair and bone formation. For example, a first layer may include a prostacyclin pharmaceutical composition and a second coating may include an active agent to decrease the degradation of the prostacyclin to provide an increased concentration locally. The present invention may also be formulated into a polymer composition that is applied to the bone junction, fracture or the bone fragments to increase the prostacyclin concentration locally. This may be in the form of an implant, biodegradable implant, a removable implant, a coating, or a combination thereof.

In such cases the composition may be formulated with a polymer, e.g., poly(vinylidene fluoride), poly(vinylidene fluoride-co-chlorotrifluoroethylene), poly(vinylidene fluoride-co-hexafluoropropylene), poly(vinylidene chloride), poly(vinyl fluoride), poly(vinyl chloride), polyvinyl acetate, polystyrene, polyisobutylene, copolymers of styrene and isobutylene, poly(styrene-b-isobutylene-b-styrene), poly(n-butyl methacrylate), poly(butyl methacrylates), polycaprolactone, poly(trimethylene carbonate), poly(L-lactide), poly (L-lactic acid), poly(lactide-co-glycolide), poly (hydroxyvalerate), poly(3-hydroxyvalerate), poly (hydroxybutyrate), poly(3-hydroxybutyrate), poly(4-hydroxybutyrate), poly(hydroxybutyrate-co-valerate), poly (3-hydroxybutyrate-co-3-hydroxyvalerate), poly(glycolide), poly(glycolic acid), poly(D,L-lactide-co-L-lactide), poly(D, L-lactide-co-glycolide), poly(D,L-lactide), poly(D,L-lactic acid), poly(glycolic acid-co-trimethylene carbonate), polyanhydride, polyorthoester, acrylic polymers and acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly (tyrosine-derived carbonates); polyacrylates, polycarbonates, poly-hydroxycarboxylic acids, polyisobutylene and ethylene-α-olefin copolymers, polymethacrylates, polyolefins, polyorthoesters, polyvinyl aromatics; polyvinyl esters, silicones, vinyl copolymers, vinyl-olefin copolymers, vinyl halide polymers and copolymers. In other embodiments, the polar polymer in the coating is selected from a group consisting of poly(ethylene-co-vinyl alcohol), poly (vinyl alcohol), ethylene vinyl alcohol copolymers, poly(2-hydroxyethyl methacrylate), poly(2-hydroxyethyl methacrylate-co-n-butyl methacrylate), poly(2-hydroxyethyl methacrylate) copolymers, poly(2-methoxyethyl methacrylate), poly(2-ethoxyethyl methacrylate), poly(2-methoxy-1-methylethyl methacrylate), poly(carbamoylmethyl methacrylate), poly(2-carbamoylethyl methacrylate), poly(1-carbamoyl-1-methylmethyl methacrylate), poly(N-(carbamoylmethyl) methacrylamide), poly(N-(1-carbamoyl-1-methylmethyl) methacrylamide), poly(phosphorylcholine methacrylate), poly(phosphoryl choline methacrylate) copolymers, PC1036, PC2126, poly(cellulose ethers), poly(amino acids), poly(ester amides), poly(ester-urethanes), poly(ether-urethanes), poly(imino carbonates), poly(acrylic acids), poly(alkylene oxalates), polyamides, poly(carboxylic acids), polycyanoacrylates, polyethers, poly(mides), poly(ketones), poly(oxymethylenes), poly(phosphazenes), poly(phosphoesters), poly(phosphoester urethanes), poly(phosphoesters), polyurethanes, poly(vinyl esters), poly(vinyl ethers), poly(vinyl ketones), starch, sodium alginate, poly(vinyl pyrrolidone), poly(vinyl methyl ether), poly(isocyanate), poly(ethylene glycol), poly(dioxanone), poly(caprolactam), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, carboxymethyl cellulose, chitin, chitosan, poly(N-acetylglucosamine), polyurethane, and PEO/PLA. In one embodiment, the polymer coating is selected from a group consisting of poly(vinyl fluoride), poly(vinyl chloride), polystyrene, polyisobutylene, copolymers of styrene and isobutylene, poly(styrene-b-isobutylene-b-styrene), poly(n-butyl methacrylate), poly(butyl methacrylates), acrylic polymers, acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly(tyrosine-derived carbonates), polyacrylates, polycarbonates, polyisobutylene and ethylene-α-olefin copolymers, polymethacrylates, polyolefins, polyorthoesters, polyvinyl aromatics, polyvinyl esters, silicones, vinyl copolymers, vinyl-olefin copolymers, and vinyl halide polymers and copolymers. The polymer coating may include multiple layers of polymers with different or similar properties depending on the specific application. In certain embodiments, the coating further comprises an optional finishing coating layer for enhancing biocompatibility and generally refers to an outermost layer, that is, a layer that is in contact with the external environment and that is coated over all other layers. The topcoat layer may be a separate distinct layer. Representative examples of the polymers of the differentially permeable topcoat layer include, but are not limited to, poly(vinyl fluoride), poly(vinyl chloride), polystyrene, polyisobutylene, copolymers of styrene and isobutylene, poly(styrene-b-isobutylene-b-styrene), poly(n-butyl methacrylate), poly(butyl methacrylates), acrylic polymers, acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly(tyrosine-derived carbonates), polyacrylates, polycarbonates, polyisobutylene and ethylene-α-olefin copolymers, polymethacrylates, polyolefins, polyorthoesters, polyvinyl aromatics, polyvinyl esters, silicones, vinyl copolymers, vinyl-olefin copolymers, and vinyl halide polymers and copolymers. In a presently preferred embodiment, the topcoat layer comprises styrene-isobutylene-styrene triblock polymer.

In such cases the composition may be formulated with biocompatible polymers. The composition can include one or more biocompatible polymers. The biocompatible polymers can be biodegradable (either bioerodable or bioabsorbable) or nondegradable and can be hydrophilic or hydrophobic. Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanoate), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one or more of the aforementioned polymers. As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

In addition the composition can be administered as in a bulk-eroding biodegradable polymer. These water compatible polymers absorb water and along with it the enzymes and other biodegradation-causing components of a physiological system. The absorbed components cause internal degradation of the polymer at a rate that competes with the rate of surface erosion. That is, degradation takes place simultaneously throughout the polymer matrix. The result can be an extremely complex drug release profile as differential degradation takes place in the bulk of the polymer and the drug is released from throughout the polymer matrix. Rather than a smooth, linear release profile such as that obtained with surface-eroding polymers, burst releases of massive amounts of drug, which can be detrimental to the health and safety of the patient, may occur. Autocatalysis compounds this situation for polyesters such as polylactides and polyglycolides. Unlike surface-eroding polymers, when bulk eroding polymers degrade to their component acids, the acids remain trapped for an extended period of time within the remaining polymer matrix wherein they catalyze further degradation, which further complicates the release profile of an incorporated therapeutic agent. For example, the amorphous biocompatible biodegradable polymer may be selected from the group consisting of poly(D,L-lactide), poly(meso-lactide), poly(L-lactide-co-glycolide), poly(D-lactide-co-glycolide)-poly(D,L-lactide-co-glycolide), poly(L-lactide-co-D,L-lactide), and poly(meso-lactide-co-glycolide). As a result the present invention provides the clinician the ability to implant the devices in their proper position and provide a source of prostacyclin to stimulate bone formation, growth and healing.

In addition the present compositions may be used in conjunction with scaffolding and implants for conducting bone formation through the scaffolding or implant. This further facilitates the healing of bone segments. In addition, the compositions and methods of enhancing bone healing may be used in conjunction with bone implants or bone grafts including grafts of artificial bone materials. The present invention provides prostacyclin compositions and methods of stimulated bone to heal with greater bone density and size.

The present invention also includes permeate, removable, or biodegradable non-structural implants to provide a source of prostacyclin to stimulate bone growth and healing. For example, the composition of the present invention may be configured as a coating on an implanted medical device to increase prostacyclin concentration and thus stimulate bone growth and healing. The prostacyclin may be deposited in a coating applied to an implanted medical device to release the prostacyclin to increase the concentration and promote bone growth.

An implant according to the present disclosure delivers a source of prostacyclin or a composition that increases prostacyclin in vivo. The implant device may be loaded or coated with the prostacyclin composition for placement in vivo. The implant device may be pre-loaded with the prostacyclin composition, thus loaded at manufacture, or may be loaded in the operating room or at the surgical site. Preloading/loading may be done with the prostacyclin composition, prostacyclin derivatives, prostacyclin precursors, prostacyclin analogues, and prostacyclin mimics, and the like. Preloading/loading may also include other active agents, for example, allograft such as DBM, synthetic calcium phosphates, synthetic calcium sulfates, enhanced DBM, collagen, carrier for stem cells, and expanded cells (stem cells or transgenic cells).

The present invention also includes extended release polymers that provide the release prostacyclin composition and/or other active agents for extended periods of time to provide an increase or constant concentration over an extended time to promote bone growth. In some instances the implant may be non-structural in nature and thus can be biodegradable to dissolve over time. In other embodiments, the implant may be coated with an extended release polymer that degrades over time after the prostacyclin composition and/or other active agents are released.

The extended release polymers may disintegrate during delivery so that it may not need to be removed after use. Examples of extended release polymers include, but are not limited to: polyesters, polyorthoesters, polyphosphoesters, polycarbonates, polyanhydrides, polyphosphazenes, polyoxalates, polyaminoacids, polyhydroxyalkanoates, polyethyleneglycol, polyvinylacetate, polyhydroxyacids, polyanhydrides, copolymers and blends thereof, and the like. In some embodiments, a biodegradable polymer may be a co-polymer of lactic and glycolic acid.

The extended release polymers also includes nondegradable polymer and include, but are not limited to: ethylene vinyl acetate copolymer (EVA), silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, polyvinyl chloride, homo- and copolymers of polyvinyl acetate, polyethylene, polypropylene, crosslinked polyesters of acrylic acid and/or methacrylic acid, alkyl acrylates such as methyl methacrylate or methyl acrylate, polyacrylic acid, polyalkacrylic acids such as polymethacrylic acid, polyvinyl alkyl ethers, polyvinyl fluoride, polytetrafluoroethylene, polycarbonate, polyurethane, polyamide, polysulphones, polystyrene, styrene acrylonitrile copolymers, poly(ethylene oxide), poly(alkylenes), poly(vinyl imidazole), poly(esters), poly(ethylene terephthalate), polyphosphazenes, and chlorosulphonated polyolefins, and combinations thereof.

In addition some embodiments may include multiple layer and multiple types of polymers to accomplish specific concentrations over given durations to promote bone growth. For example, the metal implant may include a first coating of prostacyclin composition in an extended release polymer that erodes over time to expose a second prostacyclin composition at a second concentration in an extended release polymer to provide a different final prostacyclin composition concentration. A topcoat position on the first coating that is an immediate released polymer coating that contains one or more antibiotics that are released to prevent or decrease the chance of an infection. This combination of multiple layers allows the extended release of the active agents for a predetermined duration. In addition the multiple layers allow the customization of the concentration of the active agent at any given point in the treatment. Thus it is possible to provide a first dosage of prostacyclin at the initial stage and include antibiotics and growth factors and at a later time provide a different dosage of prostacyclin near the end of the treatment regime. Thus, the instant invention provides infinite flexibility for the dosage of prostacyclin over the entire treatment regime.

The present invention may be used in conjunction with bone grafts to stimulated bone growth and healing. Autologous bone grafts, being obtained from the patient, require additional surgery and present increased risks associated with its harvesting, such as risk of infection, blood loss, and compromised structural integrity at the donor site. Bone grafts using cortical bone remodel slowly because of their limited porosity. Traditional bone substitute materials and bone chips are more quickly remodeled but cannot immediately provide mechanical support. With regards to bone grafts, allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins. Human allograft tissue is widely used in orthopaedic surgery. Non-bone composition such as a polymer composition, e.g., poly-ether-ether-ketone (PEEK) and/or other polymer compositions is also widely used in orthopaedic surgery. The present invention can be used to stimulate bone growth and healing in bone grafts.

The present invention can be used to promote growth in bone scaffolds and in conjunction with fenestration for bone ingrowth. The bone scaffold feature can be a fenestration for bone ingrowth, an elongated fenestration for bone growth, a slot fenestration for bone growth, a lumen for bone ingrowth, or a combination thereof. The bone implant can include a shape memory metal, an elastic biocompatible metal, an elastic biocompatible polymer, or a combination thereof.

In any of the present embodiment the composition may include multiple active agents, prostacyclin, prostacyclin derivatives, prostacyclin analogues, prostacyclin mimics, precursors of prostacyclin compositions and the like. The additional bioactive agents may include but not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anticholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-β); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

Prostacyclin (commonly called (Z)-5-[(4R,5R)-5-hydroxy-4-((S,E)-3-hydroxyoct-1-enyl)hexahydro-2H-cyclopenta[b]furan-2-ylidene]pentanoic acid, prostaglandin I2, or PGI2) is a prostaglandin member of the family of lipid molecules known as eicosanoids. It inhibits platelet activation and is also an effective vasodilator.

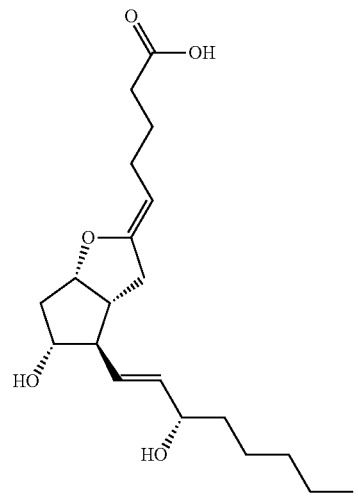 [SMILES: CCCCC[C@H](O)/C=C/[C@@H]1[C@H]2C/C(=C/CCCC(=O)O)O[C@H]2C[C@H]1O]

Examples of prostacyclin derivatives, prostacyclin analogues, prostacyclin mimics, precursors of prostacyclin compositions include but are not limited to carboprostacyclin; (5E)-5-[(3aS,4R,5R,6aS)-5-hydroxy-4-[(E,3S)-3-hydroxyoct-1-enyl]-3,3a,4,5,6,6a-hexahydro-1H-pentalen-2-ylidene]pentanoic acid; 3-(3-carboxypropyl)-7-exo-(3-hydroxy-trans-1-octenyl)-8-endo-hydroxy-cis-bicyclo[4,3,0]nona-2-ene; 3-(3-carboxypropyl)-7-exo-(3-hydroxy-4-methyl-trans-1-nonen-6-ynyl)-8-endo-hydroxy-cis-bicyclo[4,3,0]nona-2-ene; 3-(4-carboxybutyl)-7-exo-(3-hydroxy-trans-1-octenyl)-8-endo-hydroxy-cis-bicyclo[4,3,0]nona-2-ene; 3-(4-carboxybutyl)-7-exo-(3-hydroxy-4-methyl-trans-1-nonen-6-ynyl)-8-endo-hydroxy-cis-bicyclo[4,3,0]nona-2-ene; 3-(4-carboxy-1-butenyl)-7-exo-(3-hydroxy-trans-1-octenyl)-8-endo-hydroxy-cis-bicyclo[4,3,0]nona-2-ene; 3-(4-carboxy-1-butenyl)-7-exo-(3-hydroxy-4-methyltrans-1-nonen-6-ynyl)-8-endo-hydroxy-cis-bicyclo[4,3,0]nona-2-ene; [3-(3-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene]; [3-(2-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene]; (9) [3-(4-carboxybutyl)-7-exo-(3α-hydroxy-4,8-dimethyl-1-trans-octen-6-ynyl)-8-endo-hydroxy-cis-bicyclo[4,3,0]nona-3-ene]; (5Z,13E)-(8R,9S,11R,12R,15S)-9,11-15-Triacetoxy-2-(2-oxazolin-2-yl)-1-nor-5,13-prostadiene; (5Z,13E)-(8R,9S,11R,12R,15S)-2-(2-Oxazolin-2-yl)-1-nor-5,13-prostadiene-9,11,15-triol; (5Z,13E)-(8R,9S,11R,12R,15S)-2-(2-Oxazolin-2-yl)-1-nor-5,13-prostadiene-9,11,15-triol; (5Z,13E)-(8R,9S,11R,12R,15S)-2-(2-Oxazolin-2-yl)-1-nor-5,13-prostadiene-9,11,15-triol; (5Z,13E)-(8R,9S,11R,12R,15S)-2-(4,4-Dimethyl-2-oxazolin-2-yl)-1-nor-5,13-prostadiene-9,11,15-triol; (5Z,13E)-(8R,9S,11R,12R,15S)-2-(2-Thiazolin-2-yl)-1-nor-5,13-prostadiene-9,11,15-trio; 1-Decarboxy-2-(oxazolin-2-yl)-(5R,6R)-5-bromoprostaglandin-I$_1$; 1-Decarboxy-2-(oxazolin-2-yl)prostaglandin-I$_2$; 2-{4-{(E)-(1S,5S,6R,7R)-7-Hydroxy-6-[(E)-(3S,4RS)-3-hydroxy-4-methyloct-1-en-6-ynyl]bicyclo[3.3.0]octan-3-ylidene}}-butyl]-2-oxazoline; 2-{(E)-(1S,5R,6R)-7-Hydroxy-6-[(E)-(3S,4RS)-3-hydroxy-4-methyl-1-octenyl]-2-oxabicyclo[3.3.0]octan-3-ylidene}-5-(2-oxazolin-2-yl)pentanenitrile; 2-Aza-3-[1-thia-4-(2-oxazolin-2-yl)butyl]-6-(3α-acetoxy-1-octenyl)-7α-acetoxybicyclo[3.3.0]octene-2; 2-Aza-3-[1-thia-4-(2-oxazolin-2-yl)butyl]-6-(3α-hydroxy-1-octenyl)-7α-hydroxybicyclo[3.3.0]octene-2; 2-Aza-3-[1-thia-4-(2-oxazolin-2-yl)butyl]-6-(3α-trimethylsilyloxy-1-octenyl)-7α-trimethylsilyloxybicyclo[3.3.0]octene-2; 2-Aza-3-[1-thia-4-(2-oxazolin-2-yl)butyl]-6-(3α-hydroxy-1-octenyl)-7α-hydroxybicyclo[3.3.0]octene-2; 2-Aza-3-[1-thia-4-(2-oxazolin-2-yl)butyl]-6-(3α-hydroxy-4(R,S)-methyl-1-octenyl)-7α-hydroxybicyclo[3.3.0]octene-2; 2-Aza-3-[1-thia-4-(2-oxazolin-2-yl)butyl]-6-(3α-hydroxy-4,4-dimethyl-1-octenyl)-7α-hydroxybicyclo[3.3.0]octene-2; 2-Aza-3-[1-thia-4-(2-oxazolin-2-yl)butyl]-6-(3α-hydroxy-4-methyl-6,7-tetradehydro-1-nonenyl)-7α-hydroxybicyclo-[3.3.0]octene-2; 2-Aza-3-{1-thia-4-[2-(5,6-dihydro-4H-1,3-oxazin-2-yl)]-butyl}-6-(3α-hydroxy-4-phenoxy-1-butenyl)-7α-hydroxybicyclo[3.3.0]octene-2; 2-Aza-3-[1-thia-3,3-difluoro-4-(2-thiazolin-2-yl)butyl]-6-(3α-hydroxy-5-phenyl-1-pentenyl)-7α-hydroxybicyclo[3.3.0]octene-2; and 2-Aza-3-[1-thia-4-(2-imidazolin-2-yl)butyl]-6-[3α-hydroxy-4-(3-chloro phenoxy)-1-butynyl]-7α-hydroxybicyclo[3.3.0]-octene-2.

Another embodiment of the present invention includes the delivery of the prostacyclin composition locally and systemically to increase the prostacyclin to stimulate bone formation, growth and healing. In that embodiment the composition is provided locally as stated herein and administered systemically. Systemically administration may be parenterally, enterally, injected (including intravenous (IV), intramuscular (IM), and subcutaneous (SC) administration), topically or by intraarticular, intraosseous infusion. Thus allowing both a systemic and local source of the prostacyclin composition to stimulate bone formation, growth and healing. For example, the prostacyclin composition may be applied locally as a coating on an implant or in a polymer administered at the fracture and systemically through administering an oral prostacyclin composition or injected at the fracture as an injectable prostacyclin composition.

Generally, the Wnt signaling pathways are a group of signal transduction pathways made of proteins that pass signals from outside of a cell through cell surface receptors to the inside of the cell, e.g., the canonical Wnt pathway, the noncanonical planar cell polarity pathway, and the noncanonical Wnt/calcium pathway. These Wnt signaling pathways are activated by the binding of a Wnt-protein ligand to a receptor, which passes the biological signal to the protein inside the cell. Wnt signaling controls include body axis patterning, cell fate specification, cell proliferation, and cell migration. These processes are necessary for proper formation of important tissues including bone, heart, and muscle.

The balance between bone loss and deposition is important for normal bone growth and remodeling, and depends on a complex interplay between resident bone cells such as osteoclasts, osteoblasts, and osteocytes whose activities are altered by several regulatory molecules produced by such cells. Increased bone mass in human patients and mice with inactivating mutations of the sclerostin (SOST, Sost) gene whose product, a secreted glycoprotein, functions by altering Wnt, bone morphogenetic protein and other signaling pathways. Inactivating or activating mutations of the LDL receptor related protein 5 are associated with altered Wnt signaling in bone, and low or high bone mass, respectively. Sclerostin also influences Wnt activity in osteocytes in an autocrine manner, and by doing so, alters the production of prostacyclin ($PGI_2$), a cyclic prostanoid, previously known to be active in vascular tissues.

Figure 1B:
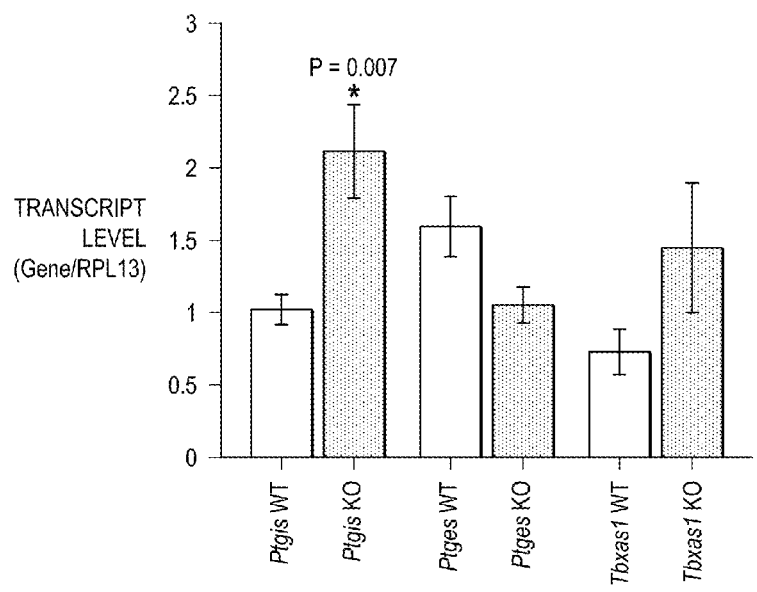
Figure 1C:
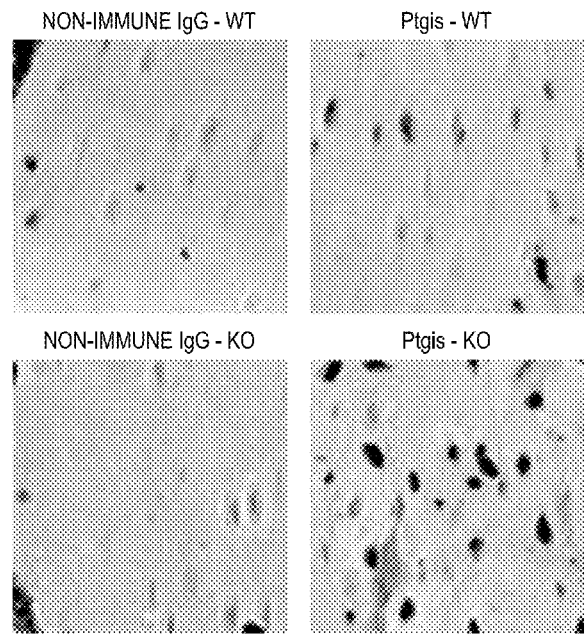

FIG. 1A-C show prostaglandin concentrations, mRNAs for prostaglandin synthases, and prostacyclin synthase in osteocytes in extracts of bones, or decalcified bone sections from Sost WT or KO mice. Specifically, FIG. 1A shows concentrations of 6-keto $PGF_{1\alpha}$, the stable metabolite of $PGI_2$, or prostacyclin, is elevated in extracts of bone from Sost KO mice compared to extracts from WT mice. Concentrations of $PGE_2$, $PGD_2$, $TXB_2$, the stable metabolite of $TXA_2$, and $PGF_{2\alpha}$ are similar in KO and WT mouse bone extracts. FIG. 1B shows concentrations of mRNA transcripts for the PG synthases, Ptgis, Ptges, and Tbxas1 show an elevation in Ptgis and little change in the other PG synthases. FIG. 1C shows Immunohistochemical detection of Ptgis in decalcified bone from Sost WT (upper panels) and Sost KO mice showing enhanced staining in KO mouse bone.

Figure 2:
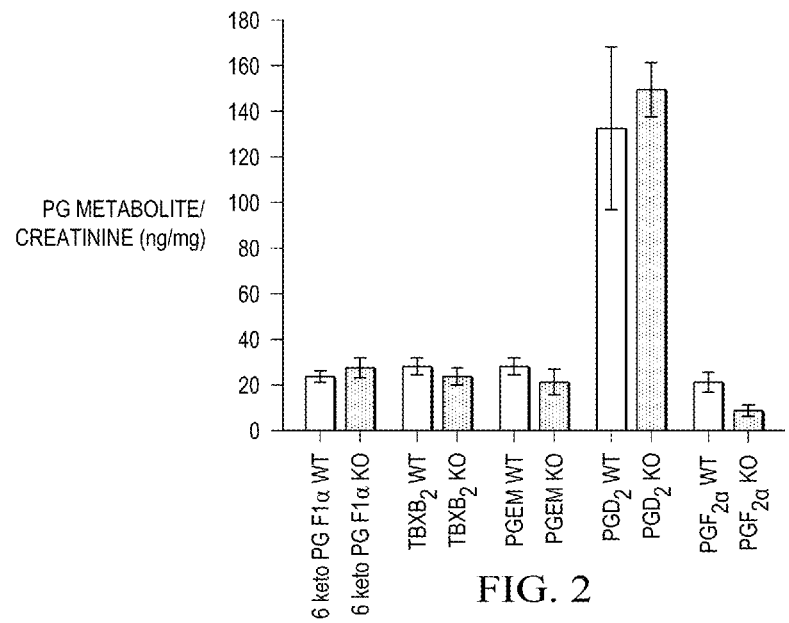
FIG. 2 shows urinary prostaglandins in Sost KO and WT mice.

Arachadonic acid (AA) the precursor to prostaglandins is converted via the cyclooxygenase pathway and the activity of cyclooxygenase 1 and 2 to prostaglandin $PGG_2$ and subsequently $PGH_2$. The latter is converted to $PGI_2$, $PGD_2$, $PGE_2$, $PGF_2$ and thromboxane $A_2$ by specific synthases; $PGF_2$ is also produced from $PGE_2$ directly. We measured concentrations of prostaglandins formed from prostaglandin $H_2$ and the concentrations of messenger RNAs of key enzymes in the prostaglandin synthetic pathway from intact bone tissue, mixed osteocytes, and clonal populations of osteocytes from Sost knockout (KO) or wild-type (WT) mice. In bone extracts, higher concentrations of 6-keto $PGF_{1\alpha}$, the stable metabolite of $PGI_2$, were detected in femoral bones from Sost KO mice compared with those measured in wild-type (WT) mice, P=0.022 (FIG. 1A). Concentrations of $PGE_2$, $PGD_2$, $TXB_2$ (the stable metabolite of $TXA_2$) and $PGF_2$, were similar in Sost KO and WT mice. The messenger RNA for the enzyme, $PGI_2$ synthase (Ptgis), was elevated in Sost KO mice compared with that measured in WT mice, P=0.007 (FIG. 1B). Messenger RNAs for $PGE_2$ synthase (Ptges) and thromboxane A synthase 1 (Tbxas1) were similar in Sost KO and WT mice. The increase in prostacyclin concentrations and Ptgis mRNA was confirmed by an increase in prostacyclin synthase (Ptgis) protein detected via immunohistochemistry in osteocytes of bones from Sost KO mice relative to osteocytes of bones from WT mice (FIG. 1C, lower right panel). Western blot analysis with Ptgis antibody showed a 57,000 kD band consistent with Ptgis protein. The data are consistent with increased prostacyclin production in bones from Sost KO mice. Urinary concentrations of 6-keto $PGF_{1\alpha}$, $PGE_2$, $PGD_2$, $PGF_2$, and $TBXB_2$ were similar in Sost KO and WT mice, reflecting the rapid metabolism of prostanoids produced in bone. These data support the well-known autocrine and/or paracrine role of prostaglandins in the regulation of cellular activities. FIG. 2 shows urinary prostaglandins in Sost KO and WT mice. Mice were kept in glass metabolic cages for 24 hours and urine was collected under mineral oil. Prostaglandins were measured using EIA as noted in the methods.

The site of sclerostin synthesis (osteocytes) was isolated and prostanoids were measured. Elevations in concentrations of 6-keto $PGF_{1\alpha}$ were noted in primary osteocytes isolated from bone of Sost KO mice (93.68±23.39 pg 6-keto $PGF_{1\alpha}$/mg protein KO osteocytes vs. 31.24±8.44 pg 6-keto $PGF_{1\alpha}$/mg protein WT osteocytes, P=0.024), whereas $PGE_2$ concentrations were similar (1.52±0.37 pg $PGE_2$/mg protein KO osteocytes vs. 1.936±0.47 pg $PGE_2$/mg protein WT osteocytes, P=0.52). To further assess the production of PG in bone we immortalized osteocytes, and examined prostaglandin metabolite concentrations in mixed and clonal populations of such cells. In mixed populations of immortalized osteocytes derived from Sost KO mice and WT mice concentrations of 6-keto $PGF_{1\alpha}$ were increased in Sost KO mice osteocytes compared to WT osteocytes (2823.509±485.643 pg/mL KO vs. 163.410±10.486 pg/mL WT, P=0.005), whereas $PGE_2$ concentrations were similar. These changes are mirrored in the amounts of mRNA for the respective synthetic enzymes.

Figure 3A:
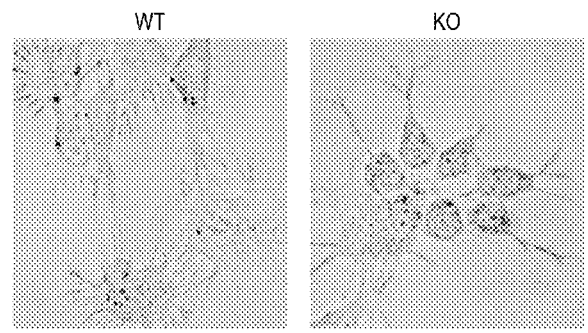
FIG. 3A shows a phase contrast microscopy image of Sost WT (left) and KO (right) osteocytes. Note dendritic extensions on cells.
Figure 3B:
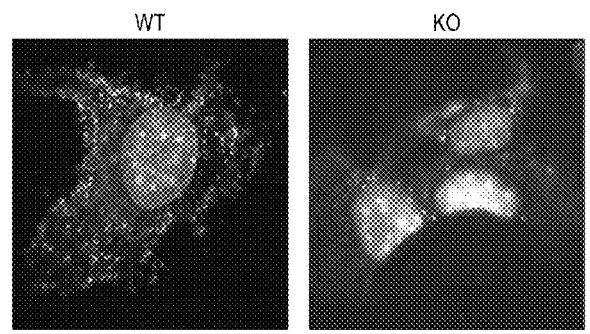
FIG. 3B shows immunostaining using an antibody directed against podoplanin (E11) in Sost WT (left) and KO (right) osteocytes.
Figure 3C:
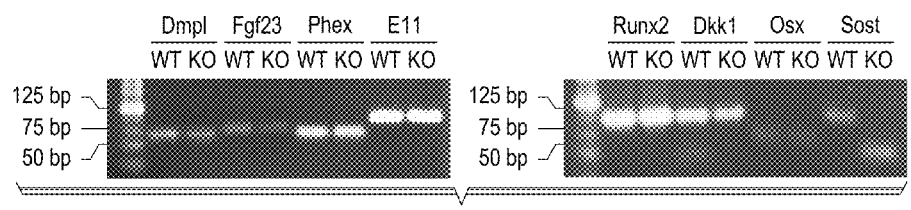
FIG. 3C shows RT-PCR products in RNA derived from Sost WT (left) and KO (right) osteocytes.

Prostaglandin production in clonal populations of Sost KO OC clone 8 and Sost WT osteocytes clone 12 displayed the phenotype characteristic of osteocytes with several dendritic cell extensions and staining for podoplanin (E11/GP38). FIG. 3A shows a phase contrast microscopy image of Sost WT (left) and KO (right) osteocytes. Note dendritic extensions on cells. FIG. 3B shows immunostaining using an antibody directed against podoplanin (E11) in Sost WT (left) and KO (right) osteocytes. FIG. 3C shows RT-PCR products in RNA derived from Sost WT (left) and KO (right) osteocytes. Specific PCR primers described below and size of the predicted product in BP is also indicated below.

| GENE SYMBOL | mRNA DESCRIPTION | PCR PRIMERS (5' TO 3') | PRODUCT (BP) | GENBANK REFERENCE |
|---|---|---|---|---|
| Dkk1 | Mus musculus dickkopf homolog 1 (Xenopus laevis) | SEQ ID NO: 1 LEFT: ccgggaactactgcaaaaat SEQ ID NO: 2 RIGHT: ccaaggttttcaatgatgctt | (94 bp) | NM_010051.3 |
| Dmp1 | Mus musculus dentin matrix protein 1 | SEQ ID NO: 3 LEFT: ggttttgaccttgtgggaaa SEQ ID NO: 4 RIGHT: catattgggatgcgattcct | (66 bp) | NM_016779.2 |
| Fgf23 | Mus musculus fibroblast growth factor 23 | SEQ ID NO: 5 LEFT: tatggatctccacggcaac SEQ ID NO: 6 RIGHT: gtccactggcggaacttg | (72 bp) | NM_022657.3 |
| Phex | Mus musculus phosphate regulating gene with homologies to endopeptidases on the X chromosome | SEQ ID NO: 7 LEFT: ctgccagagaacaagtgcaa SEQ ID NO: 8 RIGHT: aatggcaccattgaccctaa | (65 bp) | NM_011077.2 |
| Pdpn | Mus musculus podoplanin/E11 | SEQ ID NO: 9 LEFT: cagtgttgttctgggttttgg SEQ ID NO: 10 RIGHT: acctggggtcacaatatcatct | (95 bp) | NM_010329.2 |
| Runx2 | Mus musculus runt related transcription factor 2 (Runx2), transcript variant 1 | SEQ ID NO: 11 LEFT: cgtgtcagcaaagcttcttt SEQ ID NO: 12 RIGHT: ggctcacgtcgctcatct | (96 bp) | NM_001146038.1 |
| Sost | Mus musculus sclerostin | SEQ ID NO: 13 LEFT: tcctgagaacaaccagacca SEQ ID NO: 14 RIGHT: gcagctgtactcggacacatc | (94 bp) | NM_024449.5 |

| GENE SYMBOL | mRNA DESCRIPTION | PCR PRIMERS (5' TO 3') | PRODUCT (BP) | GENBANK REFERENCE |
|---|---|---|---|---|
| Sp7 | *Mus musculus* Sp7 transcription factor 7 (Osterix) | SEQ ID NO: 15 LEFT: tgcttcccaatcctatttgc SEQ ID NO: 16 RIGHT: agctcaggggggaatcgag | (66 bp) | NM_130458.3 |

The osteocyte lines expressed messenger RNAs characteristic of cells of the osteocyte lineage such as, Dmp1, Fgf23, Phex, podoplanin/E11, and Sost (Sost only in WT line). Other expressed RNAs included Runx2, Dkk1, and osterix. Prostaglandins in the cell culture media of these cells showed an great increase in 6-keto $PGF_{1\alpha}$ (3302.411±27.968 ng/mL KO OC clone 8 vs. WT clone 12, 178.889±66.486 ng/mL WT, P<0.001), whereas $PGE_2$ concentrations were slightly but statistically higher in Sost KO OC clone 8 osteocytes (1298.9±43.3 pg $PGE_2$/mL KO OC clone 8 osteocytes vs. 1093.2±31.2 pg $PGE_2$/mL WT clone 12 osteocytes, P=0.003). Analysis of mRNAs for synthetic enzymes in the PG pathway.

Figure 4A:
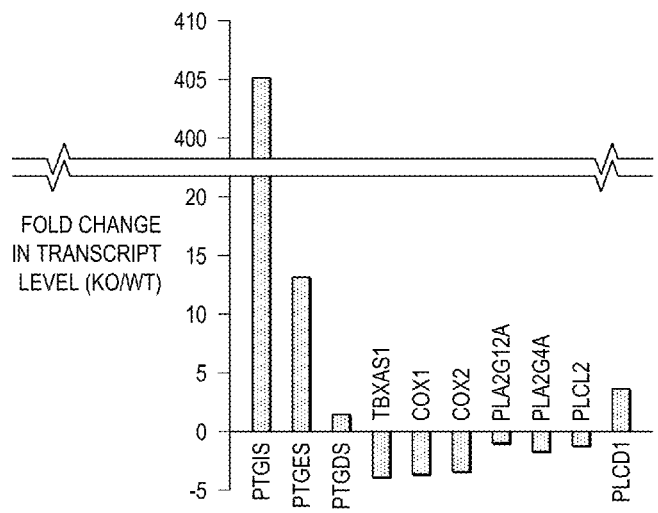
FIGS. 4A-4B shows mRNA transcripts for prostaglandin synthases, Ptgis, Ptges, Ptgds, Tbxas1, Cox1, Cox 2, Pla2g4a, Plcl2, and Plcd1 were measured in clonal Sost KO and WT osteocytes.
Figure 4B:

FIGS. 4A-4B shows mRNA transcripts for prostaglandin synthases, Ptgis, Ptges, Ptgds, Tbxas1, Cox1, Cox 2, Pla2g4a, Plcl2, and Plcd1 were measured in clonal Sost KO and WT osteocytes. Ptgis protein was measured in lystes of WT and KO osteocytes. FIG. 4A shows prostglandin synthase transcript levels expressed as a ratio of amount observed in KO/WT cells. Note that Ptgis transcripts are increased >400-fold. FIG. 4B shows Ptgis protein is greatly increased in KO osteocytes (right 4 lanes). The protein is barely detected in WT cells.

Figure 5A:
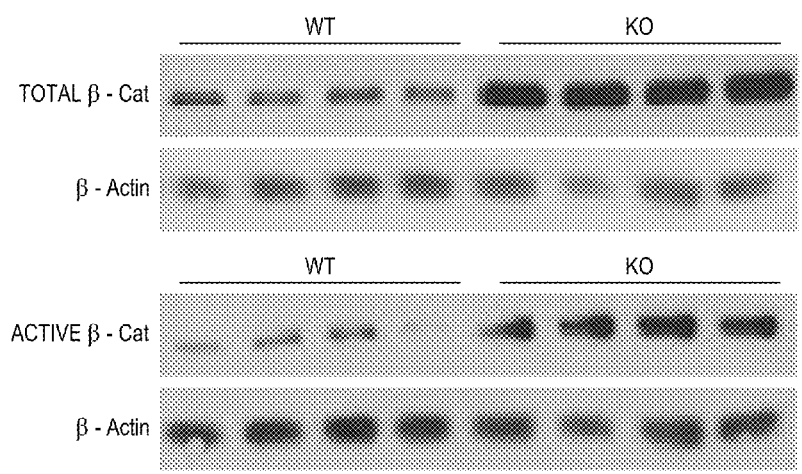

FIGS. 5A-5F shows Enhanced b-catenin and b-catenin-associated transcription is present in clonal osteocytes from Sost KO mice. FIG. 5A upper panel is an immunoblot of cellular protein from WT (right 4 lanes in panel) and KO (left 4 lanes in panel) clonal osteocytes with total b-catenin specific antibody. b-Actin was used to correct for sample loading differences in lanes. FIG. 5A lower panel is an immunoblot of cellular protein from WT (right 4 lanes in panel) and KO (left 4 lanes in panel) clonal osteocytes with non-phosphorylated (active) b-catenin specific antibody. b-Actin was used to correct for sample loading differences in lanes. FIG. 5B is an assessment of b-catenin transcript levels in WT and KO osteocytes. FIG. 5C shows b-catenin immunofluorescence (IF, red) in WT osteocyte. The nucleus of the cell is stained blue. FIG. 5D shows b-catenin IF (red) in WT osteocyte. The nucleus of the cell is stained blue. FIG. 5E panels 1-5 show localization of b-catenin (red, panel 4) and LEF (green, panel 5) in the nucleus of a clonal Sost WT osteocyte. In panel 2 and 3, co-localization of b-catenin and LEF are shown. FIG. 5F panels 1-5 show, localization of b-catenin (red, panel 4) and LEF (green, panel 5) in the nucleus of a clonal Sost KO osteocyte. In panel 2 and 3, co-localization of b-catenin and LEF are shown. More intense IF is noted in the clonal KO than in the WT clonal osteocytes. This is especially apparent in panels F3 vs. E3. Sclerostin is thought to function in osteoblasts by activating Wnt signaling. The amount of β-catenin present in Sost KO OC clone 8 and Sost WT OC clone 12 was determined. As shown in FIG. 5A and FIG. 5B, total β-catenin was increased 583%, and non-phosphorylated active β-catenin was increased 872% in Sost KO OC clone 8 vs. Sost WT OC clone 12 (P<0.001 and P=0.013, respectively). There was an increase in mRNA for β-catenin in Sost KO OC clone 8 when compared to Sost WT OC clone 12 (215% increase, P<0.001). This was associated with an increase in β-catenin present in euchromatin of Sost KO OC clone 8 (FIG. 5C) when compared to Sost WT OC clone 12 (FIG. 5B). The nuclear β-catenin co-localized with LEF over areas of euchromatin in Sost KO OC clone 8 (FIG. 5D) and Sost WT OC clone 12 (FIG. 5D). In FIG. 5E, panels 1 and 4, the localization of β-catenin in the nucleus of a clonal Sost WT osteocyte, and in FIG. 5F, panels 1 and 4, localization of β-catenin in the nucleus of a clonal Sost KO osteocyte is shown (red color). It is apparent that there is a greater amount of β-catenin localized in the nucleus of the representative clonal Sost KO osteocyte compared with the amount of β-catenin seen in the nucleus of the clonal Sost WT osteocyte. In FIG. 5, panel 5, localization of LEF in the nucleus of the same Sost WT OC osteocyte shown in panels 1 and 4, and in FIG. 1F, panel 5, localization of LEF in the nucleus of the same Sost KO osteocyte represented in panels 1 and 4 is shown (green color). It is apparent that LEF is virtually absent in the nucleus of the Sost WT OC osteocyte, whereas it is readily observed in the nucleus of the Sost KO osteocyte. FIG. 5E, panel 2, and panel 3, and FIG. 5F, panel 2, and panel 3, show merged images of β-catenin and LEF at low and high resolution in the nucleus of previously imaged Sost WT and Sost KO osteocytes. Because of a paucity of LEF nuclear localization in the imaged Sost WT osteocyte, no yellow-orange color is noted over areas of β-catenin immunostaining. On the contrary, because of the presence of increased amounts of LEF and β-catenin in the nucleus of the Sost KO osteocyte, the merged images clearly show yellow-orange areas were both proteins co-localize.

Figure 6A:
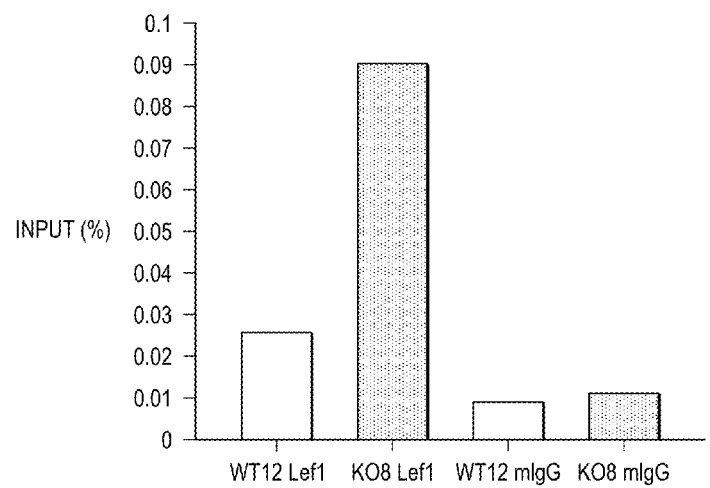
FIGS. 6A and 6B show ChIP analysis of the Lef1 sites of Sost WT OC clone 12 and Sost KO OC clone 8.
Figure 6B:
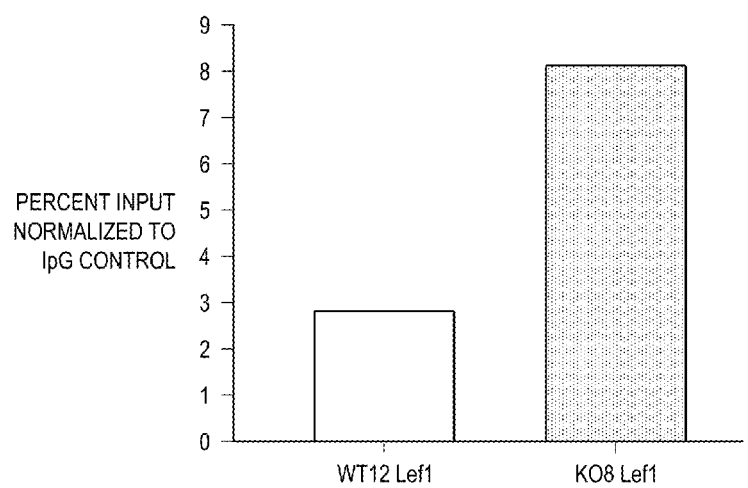

FIGS. 6A and 6B show ChIP analysis of the Lef1 sites of Sost WT OC clone 12 and Sost KO OC clone 8. FIG. 6A shows total percent input of both clones, as well as associated mouse IgG controls. FIG. 6 A shows percent Lef1 input of each clone normalized against its associated mouse IgG control counterpart. β-Catenin increases the amount of LEF localized on genes activated by Wnt signaling through the binding of LEF to specific binding sites on the DNA of activated genes. We performed chromatin immunoprecipitation experiments using Sost KO OC clone 8 and Sost WT OC clone 12, and a specific antibody against LEF, to localize LEF binding sites on the Ptgis gene. Mouse IgG was used as a control antibody. An LEF-binding site was found using in silico analysis at −1234 bp to −4567 bp on the Ptgis gene promoter. The intensity of the PCR band using specific primers upstream and downstream from this site (FIG. 6A) generated in CHIP experiments performed with Sost KO OC clone 8 was greater than those generated with Sost WT OC clone 12. These data are consistent with increased occupancy of promoter binding sites by LEF in Sost KO osteocytes. To assess whether there was an increase in β-catenin binding to LEF at the above noted DNA site, we used an activated β-catenin antibody to perform CHIP analysis with identical PCR primers. Increased amounts of the PCR product were seen when CHIP analysis was performed with a β-catenin antibody and the Sost KO OC clone 8 compared to Sost WT OC clone 12.

Figure 7A:
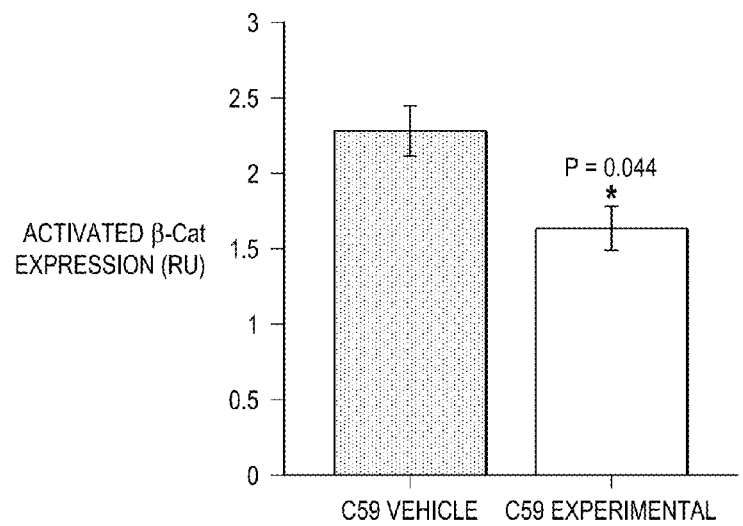
FIGS. 7A and 7B show inhibition of Wnt secretion with C-59 reduces intra-cellular activated β-catenin concentrations and 6-keto $PGF_{1\alpha}$ concentrations.
Figure 7B:
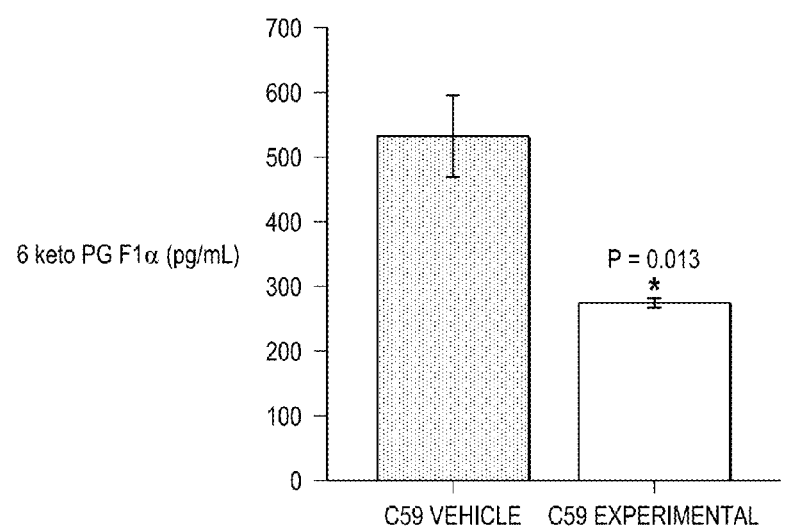

FIGS. 7A and 7B show inhibition of Wnt secretion with C-59 reduces intra-cellular activated β-catenin concentrations and 6-keto $PGF_{1\alpha}$ concentrations. FIG. 7A shows Activated β-catenin was measured in Sost KO clonal osteocytes treated with C-59 or vehicle for 48 h. FIG. 7B shows Sost KO clonal osteocytes were treated with C-59 and 48 h later, 6-keto $PGF_{1\alpha}$ was measured in culture medium. KO OC clone 8 cells were treated with a Wnt inhibitor, C-59 (2-(4-(2-methylpyridin-4-yl)phenyl)-N-(4(pyridine-3-yl) phenyl)acetamide) to assess the functional importance of β-catenin signaling in sclerostin-mediated increases in $PGI_2$ synthesis. Following treatment of cells with C59 for 48 hours there was a statistically significant decrease in β-catenin protein concentration in cells KO OC 8 cells, P<0.05 (FIG. 7A). There a concomitant decrease in 6-keto $PGF_{1\alpha}$ (536.409±60.690 pg/mL C59 vs 274.964±6.006 pg/mL vehicle, P=0.012) (FIG. 7B). Treatment with a BMP receptor inhibitor (LDN) failed to change 6-keto $PGF_{1\alpha}$ concentrations.

All animal research was conducted according to National Institutes of Health and the Institute of Laboratory Animal Resources, National Research Council guidelines. The Mayo Clinic Institutional Animal Care and Use Committee approved all animal studies. Isolation of Osteocytes from Mouse Femurs: Osteocytes were isolated from Sost KO and WT mice as described by Stern et. al. Briefly, intact femurs were aseptically isolated from eight-week-old Sost KO and WT mice. Soft tissues were removed, epiphyses were trimmed and discarded, marrow was flushed from the diaphysis with ice-cold isotonic saline, and the remaining bone was trimmed into 1 mm pieces. Bone pieces were sequentially digested by nine alternating treatments of Type 1A collagenase solution (300 AU/mL dissolved in α-Minimal Essential Medium (α-MEM)) and EDTA solution (5 mM EDTA in magnesium and calcium-free Dulbecco's Phosphate Buffered Solution (DPBS)). After the final digestion, bone pieces were placed in 6-well, collagen-treated dishes (BioCoat®, Becton Dickinson) with normal growth medium (α-MEM, 8% fetal bovine serum (FBS), 2% calf serum (CS), and 1% penicillin and streptomycin (Life Technologies)), and left undisturbed for 48 hours. Bone pieces were then removed to a separate 6-well, collagen-treated plate with growth medium for an additional 48 hours. After this incubation, cells that migrated from bone fragments were studied for osteocytic characterization. Primary isolated osteocytes were grown at 37° C., 5% $CO_2$, in normal growth medium.

To immortalize the osteocytes, an SV40 T antigen viral construct was obtained from PA317 cell supernatants. One mL of viral supernatant was added to a 35-mm dish with 2 ml of growth medium (α-MEM, 8% FBS, 2% CS, 1% P/S), and Polybrene was added to a concentration of 4 mg/ml. The virus-containing medium was left on the cells for 48 h at 34° C., 5% $CO_2$ atmosphere. The medium was then changed to growth medium containing 300 µg/ml G418 for cell selection. Cells that survived after three weeks in selection medium were assumed to have taken up the viral DNA. Immortalized osteocytes were grown at 34° C., 5% $CO_2$, in normal growth medium. Clonal populations of osteocytes from Sost KO and WT mice were generated via dilution cloning.

Preparation of Decalcified Bone for Immunohistochemistry: Femurs were decalcified for 7 days in 15% EDTA. Decalcified diaphyseal segments were embedded in paraffin and sectioned longitudinally to a thickness of 5 microns. Immunohistochemistry was performed with antibodies to prostaglandin $I_2$ synthase (Cayman Chemical 100023, 1:50 dilution), or an IgG isotype control (Vector Laboratories I-1000). Chromogens were developed using a polyvalent mouse and rabbit specific secondary HRP detection kit (Abcam, ab93697), followed by incubation in 3,3-diaminobenzidine (DAB) (Sigma Aldrich, D5905). Sections were counterstained with fast green.

All prostaglandin metabolite measurements were performed by enzyme immunoassay (EIA) using kits from Cayman Chemical (Ann Arbor, Mich.). 6-Keto prostaglandin F1α (Catalog Number 515211), prostaglandin $E_2$ (Catalog Number 514010), Prostaglandin E Metabolite (Catalog Number 514531), prostaglandin $F_{2\alpha}$ (Catalog Number 516011), prostaglandin $D_2$ (Catalog Number 512031), and thromboxane $B_2$ (Catalog Number 519031) were all performed according to kit instructions. Culture medium was diluted 1:2 in supplied buffer for each metabolite measurement, solubilized bone proteins were diluted 1:100 in supplied buffer for each metabolite measurement, and urine was diluted 1:500 in supplied buffer for each metabolite measurement.

Isolation of Media for Prostaglandin Measurements: For culture medium studies, $0.2 \times 10^6$ osteocytes from wild-type and sclerostin knock-out mice were seeded in wells of a collagen-treated 6-well BioCoat® culture dish (Becton Dickinson, Catalog Number 354400), and culture medium was collected after 48 hours, as cells reached near confluence. Isolated osteocyte culture medium was centrifuged at 100×g, diluted 1:2 in supplied buffer, and used according to manufacturer's instructions for prostaglandin measurement. Media from wild-type and Sost knock-out osteocytes was either compared directly, or normalized against a protein measurement (BCA) measured from total protein in each well of a 6-well culture plate.

Intact femurs were isolated from eight-week-old WT and Sost KO mice. After removal of epiphyses, each diaphysis was flushed with ice-cold, isotonic saline to remove marrow. De-marrowed diaphyses were weighed, snap-frozen in liquid nitrogen, ground to a powder using a mortar and pestle, and re-weighed. Frozen bone powder from each femur was re-suspended in 500 µL of modified RIPA Buffer (50 mM Tris-HCl (pH 7.4), 150 mM NaCl, 1% NP-40, 0.25% deoxycholate, 1 mM EDTA, mini-Complete Protease Inhibitor (Roche)), sonicated, and centrifuged at 14,000×g. The supernatant was isolated and used for prostaglandin measurements.

Eight-week-old male WT and Sost KO mice were placed in siliconized glass metabolic cages for 24 hours. Water was provided ad libitum, food was withheld, and a standard day/night cycle was maintained. Urine was collected under a layer of mineral oil to prevent evaporation. Urine creatinine was measured immediately upon collection on an ABX Horiba Pentra 400 (Horiba Medical), and snap frozen in liquid nitrogen prior to prostaglandin metabolite measurement.

WT and Sost KO osteocytes were grown on 12-well, collagen treated, glass bottom plates (MatTek Corporation). Upon near confluence, cells were fixed in 4% PFA for 10 minutes, washed in PBS, and blocked in 10% goat serum in PBS for 45 minutes. Primary antibody was then added ((podoplanin (8.1.1, Catalog Number sc-53533), Santa Cruz Biotechnology, Inc., 1:50 dilution in blocking buffer (3% goat serum in PBS)), (LEF-1 (N-17, Catalog Number 8591), Santa Cruz Biotechnology Inc., 1:50 dilution in blocking buffer), ((β-Catenin (Catalog Number 9562S), Cell Signaling Technologies, 1:1000 dilution in blocking buffer) overnight at 4° C. while gently shaking. After several PBS washes, secondary antibody was added (for podoplanin (Alexa Fluor 488-labeled goat anti-hamster IgG (Life Technologies), 1:200 dilution in blocking buffer), for LEF-1 (Alexa Fluor 488-labeled donkey anti-goat IgG (Life Technologies), 1:200 dilution in blocking buffer), for β-Catenin (AlexaFluor 594-labeled goat anti-rabbit IgG (Life Technologies), 1:200 dilution in blocking buffer)) for 1 hour at room temperature, with gentle agitation. Cells were then washed several times in PBS, and counterstained with Vectashield Hard Set Mounting Medium with DAPI (4',6-diamidino-2-phenylindole, Vector Laboratories).

Wells in a 6-well collagen treated plate were seeded with $0.2 \times 10^6$ sclerostin knock-out osteocytes (Clone KO8). After 48 hours, normal growth medium was removed, and cells were rinsed with PBS. Serum-free media was then added (α-MEM, 1% P/S) to the osteocytes as was well as either 100 nM of the small molecule Wnt inhibitor, C59 (2-(4-(2-methylpyridin-4-yl)phenyl)-N-(4-(pyridine-3-yl)phenyl) acetamide), or a vehicle control. After a 48 hour incubation, media was harvested from both vehicle and experimental wells and assayed for 6-keto prostaglandin $F_{1\alpha}$.

Cell lysates from 6- or 12-well plates were prepared by scraping cells in lysis buffer (0.1% SDS, 150 mM NaCl, 2 mM sodium vanadate, 0.5% sodium deoxycholate, 1% NP-40 50 mM Tris pH 8.2, 1 mM EDTA with one mini-complete protease inhibitor cocktail EDTA-free tab (Roche Diagnostics, Indianapolis, Ind.)) per 7 ml lysis solution or by direct addition of 1×SDS sample containing 5 mM EDTA and protease inhibitor as above. Protein was also prepared from RNA/Protein column flow-through by precipitation and resuspension in protein solubilization buffer-trichloro ethyl phosphine (PSB-TCEP), and protein was assayed using a trichloroacetic acid precipitation turbidity assay, bovine serum albumin (BSA) standard (Thermo Fisher Scientific, Waltham, Mass.) from the RNA/protein kit (Clontech) and with reagents supplied with the RNA/Protein kits (Clontech). Cell lysates were combined with 4×SDS sample buffer (25 mM Tris base, 20% beta-mercaptoethanol, 40% glycerol 8% sodium dodecyl sulfate, 0.04% bromophenol blue), heated to 100° C. for 5 min before loading to SDS-PAGE gels. One to five microgram protein/well or pre-stained low molecular weight standard, were loaded to mini-protean TGX any KD 15% polyacrylamide gels (Bio-Rad Hercules, Calif.). Gels were soaked in transfer buffer (25 mM Tris, 192 mM glycine, 20% methanol) for 10 min and proteins were transferred electrophoretically to polyvinylidene difluoride (PVDF) membrane (Bio-Rad). Before immunoblotting, membranes were blocked with 1% blocking reagent (Roche Diagnostics) in TBST (50 mM Tris, 150 mM NaCl, pH 7.5 with 0.05% Tween 20). for 1 h at room temperature. Membranes were probed with primary antibodies in 5% BSA, TBST: 1:1000 dilutions of non-phospho (active β-catenin) β-catenin (Ser33/37/Thr41) (D13A1) rabbit mAb (#8814), β-catenin (total β-catenin) antibody (#9562), phospho-β-catenin (Ser33/37/Thr41) antibody (#9561) (Cell Signaling Technology, Inc. Danvers, Mass.) antibody, or 1:1500 dilution prostaglandin I synthase (PGIS) (prostacyclin synthase) polyclonal antibody made in rabbit (Cayman Chemical Co. Ann Arbor, Mich.). After washing 1×10 min. with TBST, 1:2000 dilution horseradish peroxidase labeled goat anti-rabbit secondary antibody in 0.5× Roche block/TBST was applied for 1 hr (DAKO, Carpinteria, Calif.). Podoplanin (1:200 dilution) antibody (#sc-53533 Santa Cruz Biotechnology, Dallas, Tex.) was used with 1:2000 dilution anti-Syrian hamster IgG-horseradish peroxidase secondary antibody (#sc-2493 Santa Cruz Biotechnology). After washing 3×15 min with TBST blots were visualized using chemiluminescent substrate (Roche Diagnostics). PVDF membranes were washed 2×15 min at room temperature with stripping buffer (mild strip buffer (0.2 M glycine, 0.1% SDS, 1% tween 20, pH 2.2) followed by washing 2×10 min with PBS then 2×10 min with TBST, or Restore western blot stripping buffer (ThermoScientific/Pierce, Waltham, Mass.) and TBST washes or (harsh strip buffer) 50 min. at 50° C. in 2% SDS, 62.5 mM Tris pH 6.8, 114 mM β-mercaptoethanol) followed by 1-2 hr wash in running water, then TBST. Membranes were re-blocked and probed using β-actin monoclonal antibody (12E5) (#4970P Cell Signaling Technologies) in order to normalize lanes for protein loading, or probed with other primary antibodies.

Reverse transcription of isolated RNAs was carried out using oligo(dT) primers and SUPERSCRIPT® III First-Strand Synthesis System for RT-PCR. (Life Technologies, Grand Island, N.Y.) using a Perkin Elmer Cetus DNA Thermalcycler 480 (Norwalk, Conn.). PCR for osteocyte markers was carried out on T Professional thermocycler (Biometra GmbH, Göttingen, Germany) using platinum TAQ polymerase (Life Technologies, Grand Island, N.Y.). 20 μl aliquots of 50 μl PCR reactions were electrophoresed on 4% agarose, 1×TAE (Tris-acetate-EDTA buffer: 40 mM Tris, 20 mM acetic acid, and 2 mM EDTA) gels, with 1×TAE. Gels were stained by immersion in 1×TAE containing 0.5 μg/ml ethidium bromide and imaged using a Gel Doc EZ Imaging System with Image Lab software (Bio-Rad). Gels were also imaged after subsequently being destained in 1×TAE without ethidium bromide.

RNA was prepared using RNA/protein spin columns (Clontech Laboratories, Mountain View, Calif.). Lysis solution was added to live cells in 6- or 24-well plates, frozen cell pellets or frozen bone powder, prepared as detailed above. Lysates were passed through 21- and 27-gauge needles to lyse tissues and to reduce viscosity before being applied to a spin filter. Individual clarified lysates were applied to RNA spin columns for purification. RNA eluted into nuclease-free water was characterized by UV absorbance (absorbance 260 nm/280 nm ratio), quantitated and immediately frozen at −80° C.

Quantitative PCR: qPCR was carried out using a Roche LightCycler 480 QPCR apparatus in 96-well white QPCR plates and using Lightcycler 480 SYBR Green Master I (Roche Diagnostics Corp., Indianapolis, Ind.). Intron-spanning qPCR primer pairs for mouse genes were planned using the Universal Probe Library Assay Design Center (Roche Diagnostics Corporation). QPCR primers are listed below.

| GENE SYMBOL | mRNA DESCRIPTION | PCR PRIMERS (5' TO 3') | PRODUCT (BP) | GENBANK REFERENCE |
|---|---|---|---|---|
| Alox5 | Mus musculus arachidonate 5-lipoxygenase | SEQ ID NO: 17 LEFT: aggcacggcaaaaacagtat SEQ ID NO: 18 RIGHT: tgtggcatttggcatcaata | (75 BP) | NM_009662.2 |

-continued

| GENE SYMBOL | mRNA DESCRIPTION | PCR PRIMERS (5' TO 3') | PRODUCT (BP) | GENBANK REFERENCE |
| --- | --- | --- | --- | --- |
| Alox5ap | Mus musculus arachidonate 5-lipoxygenase activating protein | SEQ ID NO: 19 LEFT: catgaaagcaaggcgcata SEQ ID NO: 20 RIGHT: catctacgcagttctggttgg | (94 BP) | NM_009663.1 |
| Axin2 | Mus musculus axin2 | SEQ ID NO: 21 LEFT: cgccaccaagacctacatacg SEQ ID NO: 22 RIGHT: acatgaccgagccgatctgt | (59 bp) | NM_015732.4 |
| Ptgs1 | Mus musculus prostaglandin-endoperoxide synthase 1 (COX-1) | SEQ ID NO: 23 LEFT: cctctttccaggagctcaca SEQ ID NO: 24 RIGHT: tcgatgtcaccgtacagctc | (70 BP) | NM_008969.3 |
| Ptgs2 | Mus musculus prostaglandin-endoperoxide synthase 2 (COX-2) | SEQ ID NO: 25 LEFT: gatgctcttccgagctgtg SEQ ID NO: 26 RIGHT: ggattggaacagcaaggattt | (75 BP) | NM_011198.3 |
| Ctnnb1 | Mus musculus catenin (cadherin associated protein), beta 1, transcript variant 2 | SEQ ID NO: 27 LEFT: tgcagatcttggactggaca SEQ ID NO: 28 RIGHT: aagaacggtagctgggatca | (77 bp) | NM_001165902.1 |
| Pla2g12a | Mus musculus phospholipase A2, group XIIA, transcript variant 1 | SEQ ID NO: 29 LEFT: gactgtgacgaggagttccag SEQ ID NO: 30 RIGHT: gagctccaccgttgtctcac | (108 bp) | NM_023196.3 |
| Pla2g4a | Mus musculus phospholipase A2, group IVA (cytosolic, calcium-dependent) | SEQ ID NO: 31 LEFT: gtgaggggctttattccaca SEQ ID NO: 32 RIGHT: gaaaccccacctgaacc | (65 bp) | NM_008869.3 |
| Plcd1 | Mus musculus phospholipase C, delta 1 | SEQ ID NO: 33 LEFT: ccaactacagtcccgtggag SEQ ID NO: 34 RIGHT: ttggaagttcagagccacaa | (62 BP) | NM_019676.2 |
| Plcl2 | Mus musculus phospholipase C-like 2 | SEQ ID NO: 35 LEFT: cgctgtgtatgaaaagatcgtg SEQ ID NO: 36 RIGHT: gtgcctatgctgtgcaagtg | (75 BP) | NM_013880.3 |
| Ptgds | Mus musculus prostaglandin D2 synthase (brain) | SEQ ID NO: 37 LEFT: ggctcctggacactacaccta SEQ ID NO: 38 RIGHT: atagttggcctccaccactg | (76 BP) | NM_008963.2 |
| Ptges | Mus musculus prostaglandin E synthase | SEQ ID NO: 39 LEFT: gcacactgctggtcatcaag SEQ ID NO: 40 RIGHT: acgtttcagcgcatcctc | (101 BP) | NM_022415.3 |
| Ptgis | Mus musculus prostaglandin I2 (prostacyclin) synthase | SEQ ID NO: 41 LEFT: atgccatcaacagcatcaaa SEQ ID NO: 42 RIGHT: aaactcaggaacctctgtgtcc | (92 BP) | NM_008968.3 |
| Rpl13a | Mus musculus ribosomal protein L13A | SEQ ID NO: 43 LEFT: ccctccaccctatgacaaga SEQ ID NO: 44 RIGHT: gccccaggtaagcaaactt | (95 BP) | NM_009438.5 |

-continued

| GENE SYMBOL | mRNA DESCRIPTION | PCR PRIMERS (5' TO 3') | PRODUCT (BP) | GENBANK REFERENCE |
|---|---|---|---|---|
| Tbxas1 | *Mus musculus* thromboxane A synthase 1, platelet | SEQ ID NO: 45 LEFT: ggatgtacccaccagctttc SEQ ID NO: 46 RIGHT: acctgcagggatacgttgtc | (80 BP) | NM_011539.3 |

A SuperscriptIII RT-PCR kit (Life Technologies, Inc. Grand Island, N.Y.) was used to generate template DNA from RNA. Reverse transcribed Superscript III product was used to generate PCR products with each primer pair. Product was used to generate standard QPCR curves by serial dilution of template in each QPCR plate. QPCR data were quantitated against murine Rpl13a run for each primer pair, using software supplied with the instrument.

Chromatin Immunoprecipitation (ChIP) Assays: ChIP assays were performed on primary osteocytes isolated from $Sost^{+/+}$ and $Sost^{-/-}$ animals. Briefly, cells were treated with formaldehyde to cross-link protein and DNA complexes and sonicated to shear the chromatin. Immunoprecipitations were performed with 2 µg of antibodies specific for Lef1 or an isotype-matched IgG control (17-604, Millipore). Purified DNA was added to PCRs containing primers (SEQ ID NO: 47 5'-GCACTGAGACACGGGAAGA-3' and SEQ ID NO: 48 5'-GTCTCTGCCTCCCAAGCTC-3') that flanked the putative Lef1 binding site identified in the Ptgis promoter (SEQ ID NO: 49 5'-CCTTTGAT-3', beginning 1860 bp upstream of the translational initiation codon). ChIP DNA was measured by real-time PCR, with threshold values normalized to input DNA and the isotype control immunoprecipitation.

been seen. β-Catenin is increased in Sost knockout osteocytes and the localization of transcription factors, lymphoid-enhancer binding factor (LEF) and T-cell factor on euchromatin is also increased. The blockade of Wnt signaling reduces cellular β-catenin, LEF nuclear localization, and prostacyclin production. The Ptgis gene binds LEF in its promoter and the occupancy of binding sites is increased in Sost KO osteocytes. As such prostacyclin plays a role in bone biology and reveal a signaling relationship that can be used to enhance fracture repair and treat osteoporosis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

| Gene | WT Gene/RPL13 | SE | KO Gene/RPL13 | SE | KO/WT | p value | n | Fold Change (KO/WT) |
|---|---|---|---|---|---|---|---|---|
| qPCR Analasis, Sost Osteocytes Mixed Population | | | | | | | | |
| PTGIS | 1.0689 | 0.0216 | 107.2421 | 2.2501 | Up | <0.001 | 9 | 100.3265 |
| PTGES | 0.1716 | 0.0012 | 0.2838 | 0.0125 | Up | <0.001 | 6 | 1.6540 |
| qPCR Analysis, Sost Osteocytes KO#8 and WT#12 | | | | | | | | |
| PTGIS | 0.0022 | 0.0004 | 0.9057 | 0.0142 | Up | <0.001 | 12 | 405.4795 |
| PTGES | 0.0791 | 0.0227 | 1.0554 | 0.0499 | Up | <0.001 | 7 | 13.3477 |
| PLCD1 | 0.2605 | 0.0024 | 0.9866 | 0.0136 | Up | <0.001 | 12 | 3.7876 |
| AXIN2 | 0.1249 | 0.0075 | 0.7388 | 0.0476 | Up | <0.001 | 12 | 5.9146 |
| PTGDS | 2.3996 | 0.0979 | 3.5101 | 0.1778 | Up | <0.001 | 6 | 1.4628 |
| COX1 | 3.9415 | 0.1339 | 1.0434 | 0.0501 | Down | <0.001 | 12 | 0.2647 |
| COX2 | 4.5692 | 0.1465 | 1.2894 | 0.1015 | Down | <0.001 | 12 | 0.2822 |
| PLA2G12A | 1.0296 | 0.0100 | 1.0035 | 0.0094 | X | 0.0703 | 12 | 0.9747 |
| PLA2G4A | 1.8023 | 0.0116 | 0.9881 | 0.0103 | Down | <0.001 | 12 | 0.5482 |
| ALOX | 2.8067 | 0.1389 | 1.1607 | 0.0742 | Down | <0.001 | 12 | 0.4135 |
| ALOX5AP | 1.4576 | 0.0544 | 1.0563 | 0.0334 | Down | <0.001 | 12 | 0.7247 |
| PLCL2 | 1.3222 | 0.0275 | 0.9968 | 0.0124 | Down | <0.001 | 12 | 0.7540 |
| TBXAS1 | 4.2321 | 0.1225 | 1.0493 | 0.0328 | Down | <0.001 | 12 | 0.2479 |
| qPCR Analysis, Bone | | | | | | | | |
| PTGIS | 1.0166 | 0.1075 | 2.1113 | 0.3096 | Up | 0.0075 | 6 | 2.0769 |
| ALOX5P | 0.7323 | 0.1598 | 2.6319 | 0.4868 | Up | 0.0207 | 3 | 3.5938 |
| COX1 | 1.0565 | 0.0191 | 1.0728 | 0.0348 | X | 0.7010 | 3 | 1.0155 |
| PTGES | 1.5942 | 0.2132 | 1.0526 | 0.1314 | X | 0.0966 | 3 | 0.6602 |
| TBXAS1 | 0.7282 | 0.1607 | 1.4539 | 0.4384 | X | 0.1951 | 3 | 1.9966 |
| ALOX5 | 0.7695 | 0.0628 | 1.5397 | 0.4529 | X | 0.1674 | 3 | 2.0009 |

The balance between bone loss and deposition is regulated by chemical signaling between resident bone cells. The enhanced cellular production of prostacyclin and increased prostacyclin synthase (Ptgis) messenger RNA and protein in bone and osteocytes of sclerostin (Sost) knockout mice has All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for treating and enhancing fracture repair and bone formation comprising the steps of:
   providing a fracture comprising a bone healing interface between a first bone segment and a second bone segment in need of repair;
   providing an implant having a prostacyclin coating comprising a prostacyclin compound disposed in a polymer coating; and
   positioning the implant in a position to provide prostacyclin at the bone healing interface, wherein the prostacyclin coating releases the prostacyclin compound at the bone healing interface to enhance fracture repair and bone formation.

2. The method of claim 1, wherein the implant is a particle.

3. The method of claim 1, wherein the implant comprises a material selected from stainless steel, titanium or a combination thereof.

4. The method of claim 1, wherein the implant comprises a material selected from polyether ether ketone, polyethylene, and combinations thereof.

5. The method of claim 1, wherein the polymer coating is an extended release polymer that provides a release of the prostacyclin compound over less than 6 months.

6. The method of claim 1, wherein the prostacyclin coating comprises a prostacyclin compound disposed within multiple layers of polymer coating to provide a specific release regime over an extended period of time.

7. The method of claim 1, wherein the polymer coating comprises poly(lactide-co-glycolide).

8. The method of claim 1, wherein the prostacyclin compound is (5E)-5-[(3aS,4R,5R,6aS)-5-hydroxy-4-[(E, 3S)-3-hydroxyoct-1-enyl]-3,3a,4,5,6,6a-hexahydro-1H-pentalen-2-ylidene]pentanoic acid.

9. The method of claim 1, wherein the prostacyclin compound is selected from the group consisting of 3-(3-carboxypropyl)-7-exo-(3-hydroxy-trans-1-octenyl)-8-endo-hydroxy-cis-bicyclo[4,3,0]nona-2-ene; 3-(4-carboxybutyl)-7-exo-(3-hydroxy-trans-1-octenyl)-8-endo-hydroxy-cis-bicyclo[4,3,0]nona-2-ene; 3-(4-carboxybutyl)-7-exo-(3-hydroxy-4-methyl-trans-1-nonen-6-ynyl)-8-endo-hydroxy-cis-bicyclo[4,3,0]nona-2-ene; 3-(4-carboxy-1-butenyl)-7-exo-(3-hydroxy-trans-1-octenyl)-8-endo-hydroxy-cis-bicyclo[4,3,0]nona-2-ene; 3-(4-carboxy-1-butenyl)-7-exo-(3-hydroxy-4-methyltrans-1-nonen-6-ynyl)-8-endo-hydroxy-cis-bicyclo[4,3,0]nona-2-ene; 3-(3-oxa-4-carboxybutyl)-7-exo-(3α-hydroxy-4,8-dimethyl-1-trans-octen-6-ynyl)-8-endo-hydroxy-cis-bicyclo[4,3,0]nona-2-ene; 3-(2-oxa-4-carboxybutyl)-7-exo-(3α-hydroxy-4,8-di methyl-1-trans-octen-6-ynyl)-8-endo-hydroxy-cis-bicyclo[4,3,0]nona-2-ene; 3-(4-carboxybutyl)-7-exo-(3α-hydroxy-4,8-dimethyl-1-trans-octen-6-ynyl)-8-endo-hydroxy-cis-bicyclo[4,3,0]nona-3-ene; (5Z,13E)-(8R,9S,11R,12R,15S)-9,11-15-Triacetoxy-2-(2-oxazolin-2-yl)-1-nor-5,13-prostadiene; (5Z,13E)-(8R,9S,11R,12R,15S)-2-(2-oxazolin-2-yl)-1-nor-5,13-prostadiene-9,11,15-triol; (5Z,13E)-(8R, 9S,11R,12R,15S)-2-(4,4-dimethyl-2-oxazolin-2-yl)-1-nor-5,13-prostadiene-9,11,15-triol; (5Z,13E)-(8R,9S,11R,12R, 15S)-2-(2-thiazolin-2-yl)-1-nor-5,13-prostadiene-9,11,15-trio; 1-decarboxy-2-(oxazolin-2-yl)-(5R,6R)-5-bromoprostaglandin-I$_1$; 1-decarboxy-2-(oxazolin-2-yl)prostaglandin-I$_2$; 2-{4-{(E)-(1S,5S,6R,7R)-7-hydroxy-6-[(E)-(3S,4RS)-3-hydroxy-4-methyloct-1-en-6-ynyl]bicyclo[3.3.0]octan-3-ylidene)}-butyl}-2-oxazoline; 2-{(E)-(1S,5R,6R)-7-hydroxy-6-[(E)-(3S,4RS)-3-hydroxy-4-methyl-1-octenyl]-2-oxabicyclo[3.3.0]octan-3-ylidene}-5-(2-oxazolin-2-yl)pentanenitrile; 2-Aza-3-[1-thia-4-(2-oxazolin-2-yl)butyl]-6-(3α-acetoxy-1-octenyl)-7α-acetoxybicyclo[3.3.0]octene-2; 2-Aza-3-[1-thia-4-(2-oxazolin-2-yl)butyl]-6-(3α-trimethylsilyloxy-1-octenyl)-7α-trimethylsilyloxybicyclo[3.3.0]octene-2; 2-Aza-3-[1-thia-4-(2-oxazolin-2-yl)butyl]-6-(3α-hydroxy-1-octenyl)-7α-hydroxybicyclo[3.3.0]octene-2; 2-Aza-3-[1-thia-4-(2-oxazolin-2-yl)butyl]-6-(3α-hydroxy-4(R,S)-methyl-1-octenyl)-7α-hydroxybicyclo[3.3.0]octene-2; 2-Aza-3-[1-thia-4-(2-oxazolin-2-yl)butyl]-6-(3α-hydroxy-4,4-dimethyl-1-octenyl)-7α-hydroxybicyclo[3.3.0]octene-2; 2-Aza-3-[1-thia-4-(2-oxazolin-2-yl)butyl]-6-(3α-hydroxy-4-methyl-6,7-tetradehydro-1-nonenyl)-7α-hydroxybicyclo[3.3.0]octene-2; 2-Aza-3-{1-thia-4-[2-(5,6-dihydro-4H-1,3-oxazin-2-yl)]-butyl}-6-(3α-hydroxy-4-phenoxy-1-butenyl)-7α-hydroxybicyclo[3.3.0]octene-2; 2-Aza-3-[1-thia-3,3-difluoro-4-(2-thiazolin-2-yl)butyl]-6-(3α-hydroxy-5-phenyl-1-pentenyl)-7α-hydroxybicyclo[3.3.0]octene-2; and 2-Aza-3-[1-thia-4-(2-imidazolin-2-yl)butyl]-6-[3α-hydroxy-4-(3-chlorophenoxy)-1-butynyl]-7α-hydroxybicyclo[3.3.0]-octene-2.

10. The method of claim 1, further comprising a second polymer layer on the polymer coating wherein the second polymer layer comprises an antibiotic selected from erythromycin, bacitracin, neomycin, penicillin, polymycin B, tetracyclines, biomycin, chloromycetin, and streptomycins, cefazolin, ampicillin, azactam, tobramycin, clindamycin and gentamycin.

* * * * *